(12) United States Patent
Lei et al.

(10) Patent No.: US 8,765,483 B2
(45) Date of Patent: Jul. 1, 2014

(54) EXPLOSIVES DETECTION SUBSTRATE AND METHODS OF USING THE SAME

(75) Inventors: Yu Lei, Mansfield, CT (US); Ying Wang, Willington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 13/432,078

(22) Filed: Mar. 28, 2012

(65) Prior Publication Data

US 2012/0282705 A1    Nov. 8, 2012

Related U.S. Application Data

(60) Provisional application No. 61/470,648, filed on Apr. 1, 2011.

(51) Int. Cl.
*G01N 33/22* (2006.01)
*G01N 21/64* (2006.01)
*G01N 31/22* (2006.01)

(52) U.S. Cl.
CPC ............ *G01N 21/6428* (2013.01); *G01N 21/64* (2013.01); *G01N 21/643* (2013.01); *G01N 31/224* (2013.01); *G01N 31/227* (2013.01); *G01N 33/22* (2013.01); *G01N 33/227* (2013.01)
USPC ........... 436/110; 436/106; 436/140; 436/164; 436/165; 436/166; 436/167; 436/172; 422/82.08; 422/88

(58) Field of Classification Search
CPC ....... G01N 21/62; G01N 21/63; G01N 21/64; G01N 21/6428; G01N 21/643; G01N 2021/63; G01N 2021/64; G01N 2021/6428; G01N 21/6421; G01N 2021/6432; G01N 1/22; G01N 31/00; G01N 31/223; G01N 31/224; G01N 31/227; G01N 33/0057; G01N 33/22; G01N 33/227
USPC ......... 436/106, 110, 139, 140, 164, 165, 166, 436/167, 172, 181; 422/68.1, 82.05, 82.08, 422/83, 88, 82.09
See application file for complete search history.

(56) References Cited

U.S. PATENT DOCUMENTS

| | | | |
|---|---|---|---|
| 5,306,642 A * | 4/1994 | Reagen et al. | 436/106 |
| 8,153,065 B2 * | 4/2012 | Zang et al. | 422/82.08 |
| 8,377,713 B2 * | 2/2013 | Miller et al. | 436/172 |
| 2009/0246881 A1 * | 10/2009 | Toal et al. | 436/110 |
| 2010/0112715 A1 * | 5/2010 | Swager et al. | 436/110 |
| 2011/0057116 A1 * | 3/2011 | Trogler et al. | 250/458.1 |

OTHER PUBLICATIONS

Yuan et al (abstract from Huaxue Yanjiu Yu Yingyong, vol. 21, issue 7, 2009, pp. 1015-1018).*
Wang et al. Chapter 30 of Chromogenic Phenomena in Polymers, ACS Symposium Series, vol. 888, Aug. 17, 2004, pp. 388-399.*
Frank et al. Macromolecules, vol. 30, 1997, pp. 5397-5402.*
Bai et al. Sensors and Actuators B, vol. 130, 2008, pp. 777-782.*
Yuan et al., (Full Article in Chinese), Chemical Research and Application, vol. 21, No. 7, Jul. 2009, pp. 1015-1018.

* cited by examiner

*Primary Examiner* — Maureen Wallenhorst
(74) *Attorney, Agent, or Firm* — McCarter & English, LLP

(57) ABSTRACT

Provided herein are explosives detection substrates which include an electrospun (electro)sprayed and/or dry spun aromatic polymer, such as polystyrene, and a small molecule fluorophore. Methods for detecting an explosive material using such substrates are also provided.

27 Claims, 25 Drawing Sheets

*Figure 1*

| Compound | P$_{vap}$ (mm Hg) | Vapor Concentration (ppb) | LUMO (eV) |
|---|---|---|---|
| 2,4-DNT | 1.47 E-4 | $1.93 \times 10^2$ | -2.966 |
| 2,6-DNT | 5.67 E-4 | $7.46 \times 10^2$ | -2.166 |
| 1,2-DNB | 4.55 E-5 | 59.9 | -2.219 |
| 1,3-DNB | 9 E-4 | $1.18 \times 10^3$ | -1.505 |
| TNT | 8.02 E-6 | 10.6 | -3.483 |
| Tetryl | 5.66 E-8 | $7.45 \times 10^{-2}$ | -3.981 |
| RDX | 4.1 E-9 | $5.39 \times 10^{-3}$ | -2.531 |
| PETN | 5.45 E-9 | $7.17 \times 10^{-3}$ | -2.747 |
| HMX | 8 E-11 | $1.05 \times 10^{-4}$ | -2.721 |
| BQ | 0.9 | $1.18 \times 10^6$ | -4.853 |
| CA | 7.61 E-3 | $1.001 \times 10^4$ | -5.617 |
| TATP | 5.2 E-2 | $6.84 \times 10^4$ | 0.354 |

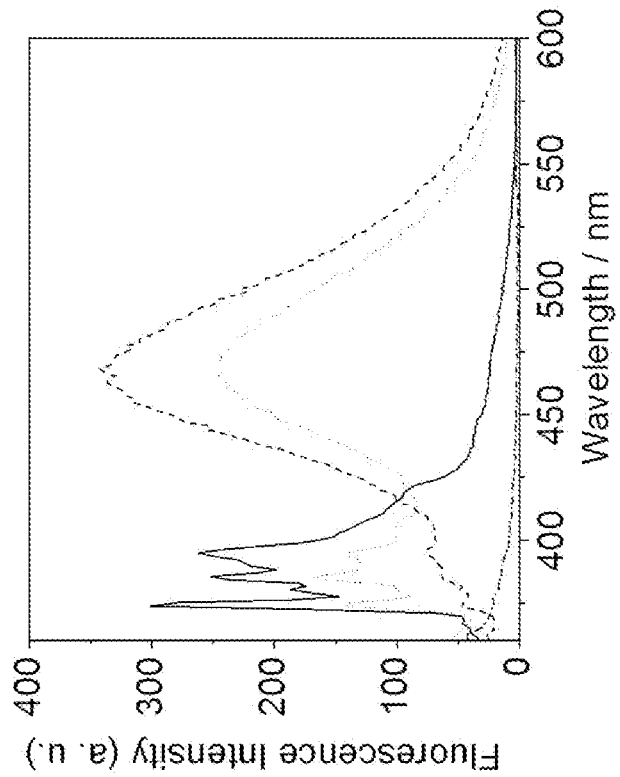
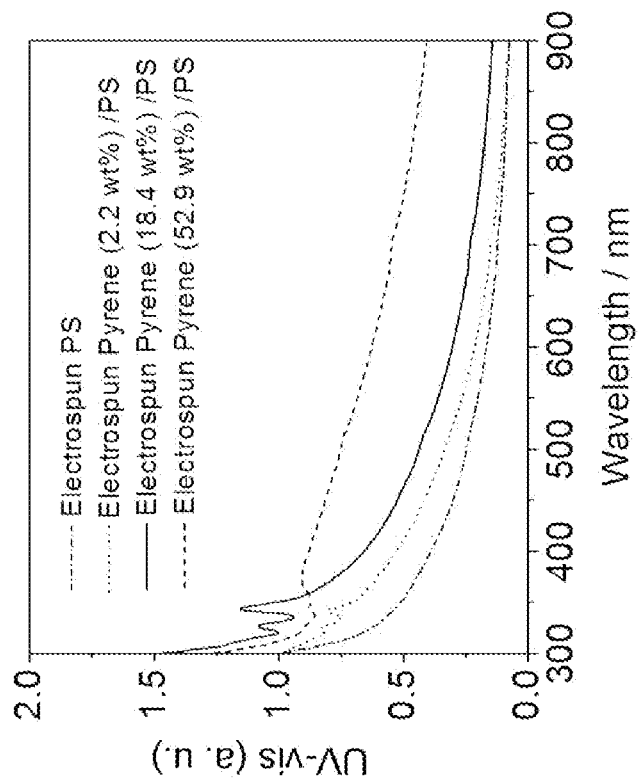
Figure 4A
Figure 4B

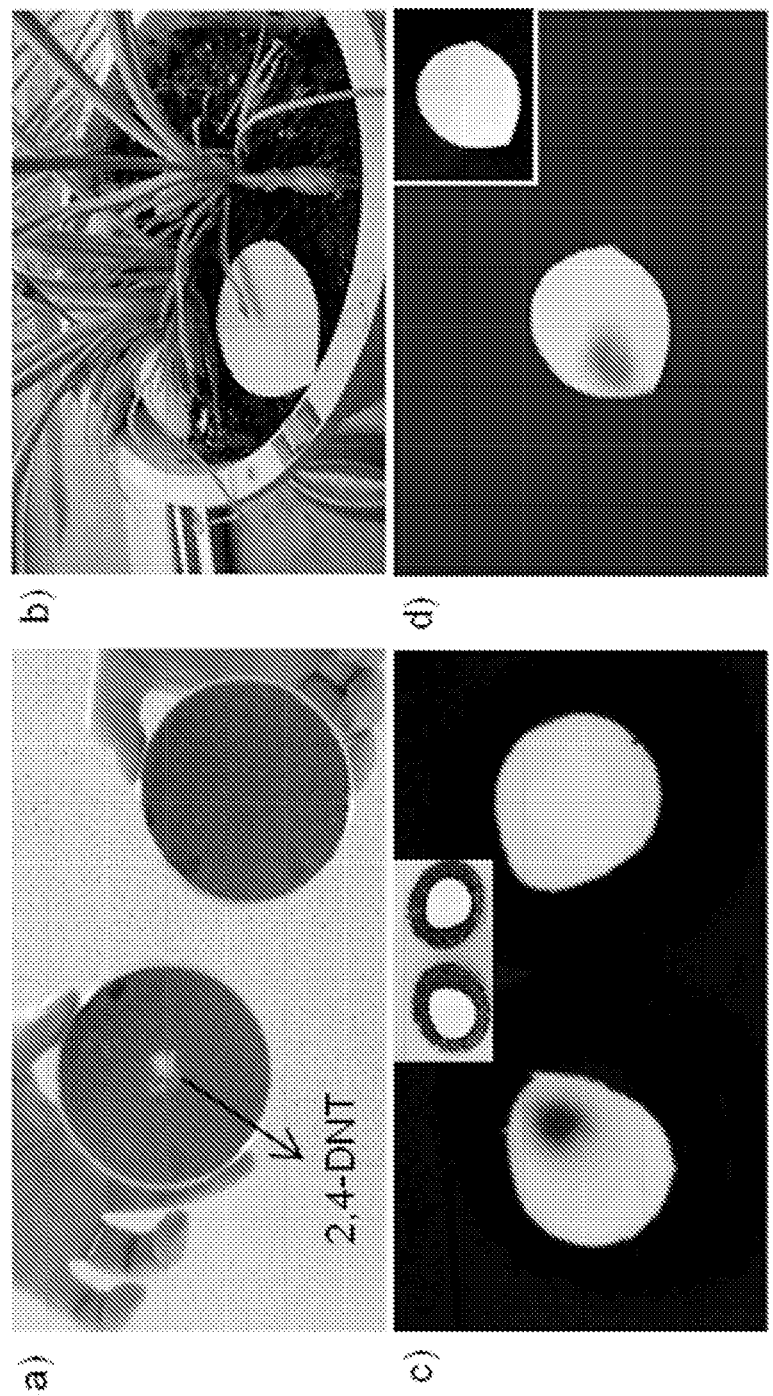
*Figure 15A-D*

EXPLOSIVES DETECTION SUBSTRATE AND METHODS OF USING THE SAME

STATEMENT REGARDING FEDERALLY SPONSORED RESEARCH OR DEVELOPMENT

This invention was made with Government support under Grant No. CMMI 0730826 from the National Science Foundation (NSF) and under Grant No. 2008-ST-108-000005 from the Department of Homeland Security (DHS). The Government has certain rights in the invention.

CROSS-REFERENCE TO RELATED APPLICATIONS

This application claims priority to U.S. Provisional Application Ser. No. 61/470,648, filed Apr. 1, 2011, the entire contents of which are incorporated herein.

BACKGROUND OF THE INVENTION

A pressing concern in anti-terrorism and homeland security is explosives detection. Most high explosives are nitro-substituted organic compounds. Typically, nitroaromatics, such as 2,4,6-trinitrotoluene (TNT) and 2,4-dinitrotoluene (2,4-DNT), are the primary military explosives and also the principle components in the unexploded landmines worldwide. Nitramines and nitrate esters (e.g. 3,5-trinitroperhydro-1,3,5-triazine (RDX) and pentaerythritol tetranitrate (PETN)) are the main components of highly energetic plastic explosives, such as C-4 (91% RDX) and Semtex (40-76% PETN). The demands of detecting hidden or buried explosives have led to an intense interest in low cost and ultrasensitive explosives detection techniques. Nitro explosives are also extremely sensitive to shock, friction and impact. Therefore, detection methods that permit contact-free analysis are desirable.

Several methods are currently available for the detection of explosives. The EPA approved standard technology for trace nitroaromatic and nitramine detection is EPA protocol SW-846 Method 8330a (http://www.epa.gov/osw/hazard/testmethods/sw846/online/8_series.htm). This method involves reverse-phase HPLC with UV detection. Detection technologies based on sensors have also been developed over the past decade. These technologies, which are typically patterned after the dog's or human's olfactory senses, can contain multiple receptors (or sensor arrays). Each vapor introduced to the electronic nose causes some or all of the sensor elements to respond differentially, producing unique response patterns that encode each vapor. In combination with pattern-recognition software, an artificial olfaction system is created that can recognize simple or complex odors. Another technique for nitro-explosive vapor detection involves ion mobility spectrometry (IMS) and gas chromatography coupled with mass spectrometry (GC-MS). Yet, these systems suffer from not satisfying one or more of the characteristics desired in a field detector, including portability, ease of use, real-time measurements, high sensitivity, selectivity for a range of compounds, high throughput capabilities, harmlessness to operator or bystanders, low cost, and applicability to solids, gases and liquids.

The stability of energetic materials is often assessed by their trigger linkage, which is generally the C—$NO_2$ bond in nitro explosives. Consequently, a high nitro substitution has become an important characteristic and renders nitro explosives electrophilic. This characteristic also allows quenching of fluorophores through photoinduced electron transfer. Fluorescent conjugated polymers have been considered a leading structure in new explosives detection techniques due to their efficient exciton migration along the polymer chains. These polymers allow for fluorescence quenching over a long range by a single quencher-binding, or called "molecular wire" signal amplification. The application of these techniques to vapor detection of explosives, however, remains a challenge because most explosive materials have ultra-low volatility (e.g. the saturation vapor concentrations for HMX, RDX, and PETN are 0.1, 5 and 7 ppt, respectively), unfavorable reduction potential, and the lacking of conjugated electrons to engage in π-stacking.

Solid-state sensing materials have been used for vapor detection. The performance of most fluorescent sensory materials is limited by film thickness. The diffusion of analyte vapors in non-porous rigid films is slow. It has been reported that a spin-coated conjugated polymer film achieves its optimum quenching efficiency towards TNT vapor with an ultrathin film (ca. 2.5 nm) and experiences a sharp drop in quenching efficiency at films thicker than 25 nm. See J. S. Yang, T. M. Swager, J. Am. Chem. Soc. 1998, 120, 5321. To reduce the dependence of sensing performance on film thickness, a sensor based on a highly porous nanostructure with a large surface-to-volume ratio, inherent high porosity, and easy accessibility of sensing materials is needed.

SUMMARY OF THE INVENTION

The present teachings are directed, at least in part, to substrates and methods for quick, inexpensive and highly sensitive explosives detection, which are capable of detecting a wide range of explosive materials. The explosives detection substrates of the present teachings are based, at least in part, on polymeric carriers which include small molecule fluorophores. Although the small molecule fluorophores are not covalently linked to the polymeric carrier, the substrates are still very highly sensitive, possibly due to the arrangement of the π electron systems. Moreover, the substrates and methods of the present teachings are, as discussed in more detail herein, highly effective in detecting not only higher vapor pressure explosives, such as TNT, but also very low vapor pressure explosives, such as HMX, RDX, or PETN.

Accordingly, in some embodiments, the present teachings provide explosives detecting substrates, such substrates may include an aromatic polymer and a small molecule fluorophore. The aromatic polymer may include, for example, a plurality of structural units corresponding to Formula (I):

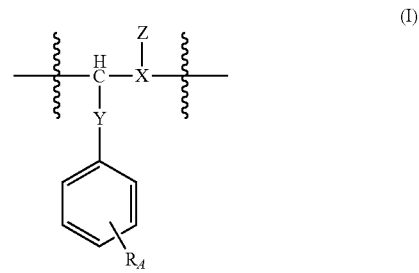

(I)

wherein $R_A$ is selected from hydrogen, cyano, methyl, —$B(OH)_2$, —C(O)H, —$C(O)CH_3$, —C(O)OH, —C(O)$OCH_3$, and $SO_3$;

wherein X is —$(CH_2)_n$—, n is 1-5, and at least one —$(CH_2)$— unit may be optionally replaced with a —(NH)— or and —O— group;

wherein Y is selected from a bond and —(CH$_2$)$_m$—, and m is 1-3; and wherein Z is selected from hydrogen, methyl, ethyl, propyl, isopropyl, (O), —C(O)H, —CH$_2$—C(O)H, —C(O)CH$_3$, —C(O)OH, or —C(O)OCH$_3$.

In some embodiments, the aromatic polymer is polystyrene. In other embodiments the aromatic polymer is polystyrene sulfonate.

The small molecule fluorophore can include, for example, an aromatic multi-ring hydrocarbon, an aromatic multi-ring heterocycle, or a mixture thereof. In some embodiments, the small molecule fluorophore is at least one fluorophore selected from compounds of Formulas (II) or (III):

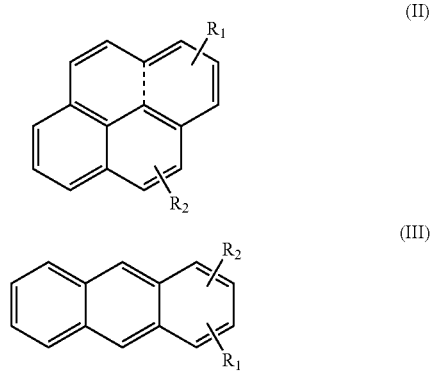

wherein R$_1$ and R$_2$ are each independently selected from hydrogen, cyano, C$_{1-4}$ alkyl, —B(OH)$_2$, —C(O)H, —C$_{1-4}$ alkyl-C(O)H, —C(O)CH$_3$, —C$_{1-4}$ alkyl-C(O)CH$_3$, —C(O)OH, —C$_{1-4}$ alkyl-C(O)OH, —C(O)OCH$_3$, —C$_{1-4}$ alkyl-C(O)OCH$_3$ and —C$_{1-4}$ alkyl-C(O)O-succinimide.

In some embodiments, the small molecule fluorophore is selected from pyrene, 1-pyrenebutyric acid, pyrene-1-boronic acid, 1-pyrenebutyric acid N-hydroxysuccinimide ester, anthracene, and mixtures thereof. In some embodiments, the small molecule fluorophore comprises pyrene.

In some embodiments, the small molecule fluorophore is substantially evenly distributed throughout the substrate. In some embodiments, the small molecule fluorophore is present in the substrate at about 15% to about 25%, by weight. In some embodiments, the substrate is non-woven. In some embodiments, the substrate exhibits a porosity of at least about 5%. In some embodiments, the substrate exhibits a surface to volume ratio of at least about 10 mm$^2$/mm$^3$. In some embodiments, the substrate is capable of detecting an explosive material in an amount less than about 1 ppb (e.g. less than about 0.01 ppb). In some embodiments, the substrate is capable of detecting an explosive material having a vapor pressure of less than about 1×10$^{-6}$ Torr at room temperature/atmospheric pressure (e.g. less than about 1×10$^{-7}$ Torr at room temperature/atmospheric pressure). In some embodiments, the substrate is capable of detecting an explosive material in less than about 30 seconds.

In some embodiments, the substrate comprises an electrospun polystyrene-pyrene matrix.

The present teachings are also directed to an explosives detecting substrate comprising an aromatic polymer in the form of electrospun or dry spun fibers, (electro)sprayed particles or fibers, or mixtures thereof; and a small molecule fluorophore, wherein the fluorophore is non-covalently bound to the polymer.

In some embodiments, the present teachings provide methods for detecting an explosive material. Such methods may generally include contacting the explosives detecting substrate described herein with an explosive material for at least about 1 second; measuring the amount of fluorescence emitted by the explosives detecting substrate; and comparing the amount of fluorescence with a suitable control. An explosive material can be detected where the fluorescence of the explosives detecting substrate is less than the fluorescence of the suitable control.

In some embodiments, the explosive material comprises a low vapor pressure explosive material. In some embodiments, the explosive material has a vapor pressure of less than about 1×10$^{-6}$ Torr at room temperature/atmospheric pressure. The explosive material can include, for example, octahydro-1,3,5,7-tetranitro-1,3,5,7-tetrazocine (HMX), hexahydro-1,3,5-trinitro-1,3,5-triazine (RDX), 1,3,5-trinitrobenzene (TNB), 1,3-dinitrobenzene (DNB), methyl-2,4,6-trinitrophenylnitramine (Tetryl), nitrobenzene (NB), 2,4,6-trinitrotoluene (TNT), picric acid (PA), 2,4-dinitrotoluene (24DNT), 2,6-dinitrotoluene (26DNT), o-nitrotoluene (2NT), m-nitrotoluene (3NT), p-nitrotoluene (4NT), nitroglycerin (NG), 4-amino-2,6-dinitrotoluene (4-Am-DNT), 2-amino-4,6-dinitrotoluene (2-Am-DNT), pentaerythritol tetranitrate (PETN) and 2,3-dimethyl-2,3-dinitrobutane (DMNB).

In some embodiments, the method is capable of detecting an explosive material in an amount less than about 1 ppb. In some embodiments, the method is capable of detecting an explosive material in an amount less than about 0.01 ppb.

In some embodiments, the explosive material comprises methyl-2,4,6-trinitrophenylnitramine (Tetryl). In some embodiments, the explosive material comprises hexahydro-1,3,5-trinitro-1,3,5-triazine (RDX). In some embodiments, the explosive material comprises 2,4-dinitrotoluene (24DNT). In some embodiments, the explosive material pentaerythritol tetranitrate (PETN).

In some embodiments, measuring the amount of fluorescence emitted by the explosives detecting substrate comprises measurement of emission with a fluorimeter.

In other embodiments, measuring the amount of fluorescence emitted by the explosives detecting substrate comprises measurement of emission with a naked eye and a handheld UV light.

In some embodiments, the present teachings provide methods for forming an explosives detecting substrate. The methods generally include electrospinning, or (electro)spraying, an aromatic polymer in the presence of a small molecule fluorophore such that an explosives detecting substrate is formed.

In some embodiments, the electrospinning, or (electro)spraying step, comprises the application of a voltage, wherein the voltage ranges from about 0 to about 25 kV.

In some embodiments, the present teachings provide sensors which include the explosives detecting substrate described herein. In some embodiments, the sensor also includes a complementary analytical device, such as a fluorimeter, a mass spectrometer and/or an absorption spectrometer.

BRIEF DESCRIPTION OF THE FIGURES

FIG. 1 is a table showing vapor pressures, saturated vapor concentrations, and LUMO energies of analytes and interferences. Saturated vapor concentrations are calculated from vapor pressure at 25° C., and LUMO energies for various explosives and interferences are either adopted from literature or calculated at the B3LYP/6-31G* level of theory.

FIGS. 4A-B are graphs showing the absorbance (A) and fluorescence emission (B) spectra of exemplary electrospun pyrene/PS substrate of the present teachings with varying pyrene contents.

FIG. 11A shows the time-dependent fluorescence intensity upon exposure equilibrium 2,4-DNT vapor (the exposure time from top to bottom are 0, 0.6, 1.2, 1.8, 2.4, 3, 3.6, 4.2, 4.8, and 6 min, respectively). FIG. 11B shows the effect of substrate thickness on time-dependent fluorescence quenching efficiency (1 μm, 3 μm, 6 μm, 9 μm, and 15 μm). FIG. 11C shows the time-dependent fluorescence quenching efficiency for different analytes (saturated vapors, except 50 ppm for $NO_2$) on 1-μm and 3-μm thick substrates.

FIGS. 15A-E show an above-ground detection of buried 2,4-DNT using the electrospun pyrene/PS/TBAH substrates (3-μm thick, figures are taken at 30 min exposure time for a better visibility). FIG. 15A shows an optical images of soil with (left) and without (right) buried 2,4-DNT in Petri dishes. FIG. 15B shows optical images of soil with buried DNT in a flower pot. FIG. 15C shows a UV ($\lambda_{ex}$ 275 nm) excited image of electrospun sensing substrates on buried DNT in a Petri dish after 30 min exposure time. FIG. 15D shows a UV ($\lambda_{ex}$ 275 nm) excited image obtained from the test of electrospun sensing substrate on 2,4-DNT buried in a flower pot after 30 min. Insets in FIG. 15C-D are the bright-field images of same membranes after detection. FIG. 15E shows the detection of particulate explosives contaminated hand using the electrospun pyrene/PS/TBAH substrates.

DETAILED DESCRIPTION OF THE INVENTION

Figure 2:
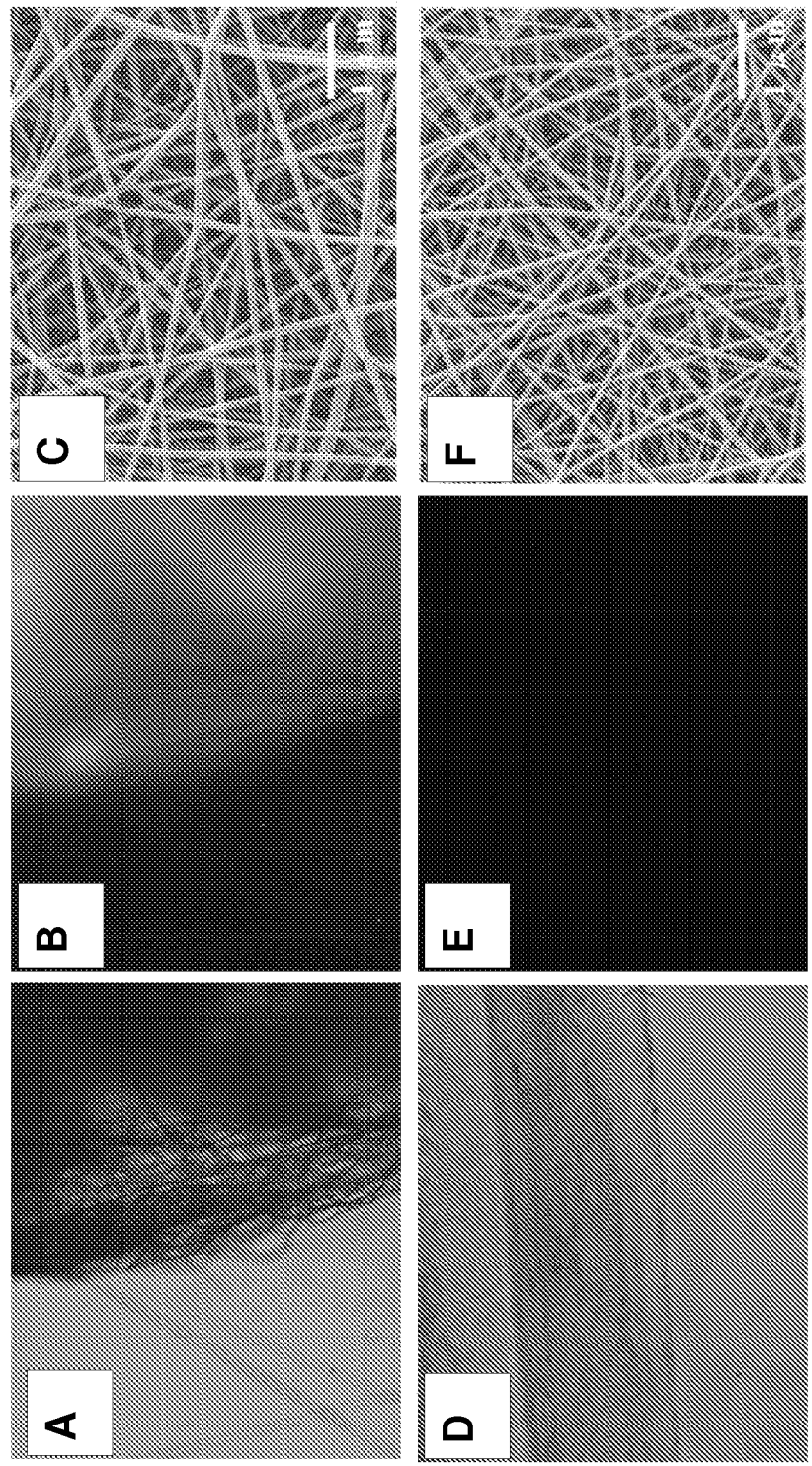
FIGS. 2A-F are photos showing (A) bright-field microscopy, (B) fluorescence microscopy, and (C) SEM images of exemplary electrospun pyrene/PS substrates of the present teachings as well as (D) bright-field microscopy, (E) fluorescence microscopy, and (F) SEM images of a control electrospun polystyrene (PS) nanofibrous substrate.

The present teachings provide substrates and methods for detecting explosive materials. The present teachings are based, at least in part, on the presence of co-facial interactions between the π-orbitals of an aromatic polymer and the π-orbitals of small molecule fluorophores. Such co-facial interactions are typically referred to as "π-π stacking" or "π-π interactions." By creating favorable π-π interactions (e.g. during electrospinning) the aromatic polymer is able to strongly "bind" with small molecule fluorophores without the need for ionic or covalent interactions (e.g. non-covalent binding). The π-π stacking arrangement can also facilitate energy transfer between donor and acceptor species as well as long-range exciton migration along the aromatic polymer chain. This, in turn can increase not only the likelihood, but also the amplitude of quenching.

Without wishing to be bound by any particular theory, it is believed that the substrates as described herein may provide advantages over presently utilized methods, including for example, mass-production with low cost, user-friendliness (e.g. only handheld UV light required), speed of quenching and detection, as well as the possibility of direct electrospinning or (electro)spraying onto a target environment. Importantly, the methods and substrates of the present teaching are able to detect explosives over a large range of vapor pressures, which is often not possible with conventional detection systems. Moreover, substrates and methods of the present teachings can be used alone with direct visualization (e.g. under UV light), or can be used in combination with any number of detection systems, such as those which employ fluorimetry, absorption spectroscopy, mass spectrometry and/or other methods known to those skilled in the art. Such combinations can, for example, further increase the sensitivity of the substrates and methods of the present teaching.

DEFINITIONS

In order to more clearly and concisely describe the subject matter of the claims, the following definitions are intended to provide guidance as to the meaning of terms used herein.

As used herein, the articles "a" and "an" mean "one or more" or "at least one," unless otherwise indicated. That is, reference to any element of the present teaching by the indefinite article "a" or "an" does not exclude the possibility that more than one of the element is present.

Certain values and ranges are recited in connection with various embodiments of the present teaching. It is to be understood that all values and ranges which fall between the values and ranges listed are intended to be encompassed by the present teaching unless explicitly stated otherwise.

The phrase "and/or," as used herein, should be understood to mean either or any combination of the elements recited. Other elements may optionally be present other than the elements specifically identified by the "and/or" clause, whether related or unrelated to those elements specifically identified unless clearly indicated to the contrary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements.

As used herein, "alkyl" groups include saturated hydrocarbons having one or more carbon atoms, including straight-chain alkyl groups (e.g. methyl, ethyl, propyl, butyl, pentyl, hexyl, methylene, ethylene, propylene, butylene, pentylene, hexylene, etc.), branched-chain alkyl groups (isopropyl, tert-butyl, sec-butyl, isobutyl, etc.), and alkyl-substituted alkyl groups (e.g. alkyl-substituted cycloalkyl groups and cycloalkyl-substituted alkyl groups). The term "$C_{1-6}$" as in "$C_{1-6}$ alkyl" means alkyl groups containing 1 to 6 carbon atoms. The terms "alkenyl" and "alkynyl" refer to unsaturated hydrocarbon groups analogous to alkyls, but which contain at least one double or triple carbon-carbon bond respectively. As used herein, "cycloalkyl" groups (or "alicyclic" or "carbocyclic" groups) include cyclic alkyl groups (e.g. cyclopropyl, cyclopentyl, cyclohexyl, etc.).

The term "aryl" refers to a carbocyclic aromatic ring system. The term "heteroaryl" includes unsaturated closed ring structures analogous to aryl groups in which one or more of the carbon atoms in the ring is an element other than carbon, for example, nitrogen, sulfur, or oxygen. Exemplary heteroaryl groups include, but are not limited to, pyrrolyl, pyridyl, isoquinolyl, quinolyl, purinyl, and furyl.

Explosives Detection Substrate

In some embodiments, the present teachings provide an explosives detection substrate. The substrate includes, for example, an aromatic polymer and a small molecule fluorophore. The substrate may be formed by electrospinning or (electro)spraying. The term "electrospun" or "(electro) sprayed" when used in reference to polymers are recognized by persons of ordinary skill in the art and includes fibers produced by the respective processes. Such processes are described in more detail infra. In some embodiments, the present teachings provide an electrospun explosives detection substrate which includes an aromatic polymer and a small molecule fluorophore.

In other embodiments, the substrate (e.g. particles or fibers) may be formed by conventional spinning or spraying techniques, such as dry spinning.

As used herein, the term "aromatic polymer" refers to an unconjugated polymer having a plurality of pendant aromatic groups. That is, aromatic polymers include polymers having a plurality of aromatic groups which are substituents on an unconjugated polymer backbone. For example, aromatic polymers include polymers having following schematic representation:

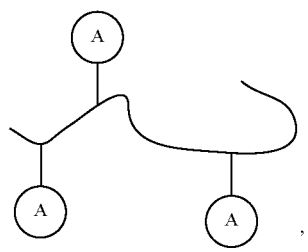

wherein the curved line represents the backbone (e.g., a carbon chain, a polyethylene glycol backbone, a peptide backbone, a protein backbone, or mixtures thereof) and (A) represents aromatic groups, such as aryl groups (e.g., $C_{5-10}$ aryl groups) or heteroaryl groups (e.g., $C_{5-10}$ heteroaryl groups). In some embodiments, the polymer backbone may not comprise any aromatic or cyclic rings. In other embodiments, the aromatic polymer has a low background signal, substantially no background signal, or a background signal which does not substantially interfere with the signal generated by the fluorophore or the fluorophore within the explosives detection substrate, either in the presence or in the absence of analyte.

In some embodiments, the backbone can be a biopolymer, such as a protein or peptide backbone, with pendant aromatic groups, such as the aromatic groups present herein or contained within, for example, phenylalanine or tryptophan residues. In some embodiments, at least 10% of the residues in the biopolymer include an aromatic group. In some embodiments, at least 25%, at least 50%, at least 75%, at least 90%, at least 95% or about 100% of the residues in the biopolymer include an aromatic group.

In some embodiments, the aromatic groups of the aromatic polymer are substituted (e.g. with one substituent). The term "substituted" means that the moiety has substituents placed on the moiety other than hydrogen (i.e. in most cases, replacing a hydrogen) which allow the molecule to perform its intended function. It will be understood that "substitution" or "substituted with" includes the implicit proviso that such substitution is in accordance with the permitted valence of the substituted atom and the substituent, and that the substitution results in a stable compound (e.g. which does not spontaneously undergo transformation such as by rearrangement, cyclization, elimination, etc.). Suitable substituents are known to a person of ordinary skill in the art and include, but are not limited to, alkyl (e.g. $C_{1-6}$ alkyl), alkenyl (e.g. $C_{2-6}$ alkenyl), alkynyl (e.g. $C_{2-6}$ alkynyl), cycloalkyl (e.g. $C_{3-7}$ cycloalkyl), aryl (e.g. $C_{5-7}$ aryl), halo, hydroxyl, amino, thio, —B(OH)$_2$, —C(O)H, —C(O)—$C_{1-6}$ alkyl, —C(O)OH and —C(O)O—C$_{1-6}$ alkyl. In some embodiments, the substituent is an electron donating group. Electron donating groups are known to those of skill in the art.

In some embodiments, the aromatic polymer includes a plurality of structural units corresponding to Formula (I):

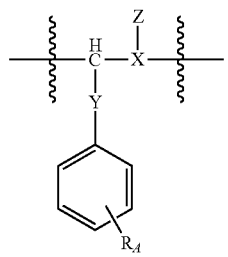

(I)

wherein R$_A$ is selected from hydrogen, cyano, alkyl, —B(OH)$_2$, —C(O)H, —C(O)-alkyl, —C(O)OH, —C(O)O-alkyl and SO$_3$;

wherein X is —(CH$_2$)$_n$—, n is 1-5, and at least one —(CH$_2$)— unit may be optionally replaced with a —(NH)— or and —O— group;

wherein Y is selected from a bond and —(CH$_2$)$_m$—, and m is 1-3; and wherein Z is selected from hydrogen, methyl, ethyl, propyl, isopropyl, (O), —C(O)H, —CH$_2$—C(O)H, —C(O)CH$_3$, —C(O)OH, or —C(O)OCH$_3$.

That is, in some embodiments, the explosives detection substrate includes an polymer which comprises a plurality of structural units corresponding to Formula (I), above; and a small molecule fluorophore.

It is to be understood that the symbol "$\xi$" denotes the position of attachment of the structural unit of Formula (I) to other structural units in the polymer.

In some embodiments, R$_A$ is selected from hydrogen, cyano, C$_{1-4}$ alkyl, —B(OH)$_2$, —C(O)H, —C(O)—C$_{1-4}$ alkyl, —C(O)OH, —C(O)O—C$_{1-4}$ alkyl and SO$_3$. In some embodiments, R$_A$ is selected from hydrogen, cyano, methyl, —B(OH)$_2$, —C(O)H, —C(O)CH$_3$, —C(O)OH, —C(O)OCH$_3$ and SO$_3$. In some embodiments, R$_A$ is selected from hydrogen, methyl and SO$_3$. In some embodiments, R$_A$ is hydrogen.

In some embodiments, X is selected from —(CH$_2$)—, —(CH$_2$)—(CH$_2$)—, and —(CH$_2$)—(CH$_2$)—(CH$_2$)—, wherein at least one —(CH$_2$)— unit may be optionally replaced with a —(NH)— or and —O— group. In some embodiments, X is selected from —(CH$_2$)—, —(CH$_2$)—(CH$_2$)—, —(CH$_2$)—(CH$_2$)—(CH$_2$)— and —(CH$_2$)—(CH$_2$)—(NH)—. In some embodiments, X is —(CH$_2$)—.

In some embodiments, Y is selected from bond and —(CH$_2$)—. In other embodiments, Y is a bond.

In some embodiments, Z is selected from hydrogen, methyl, ethyl, propyl, and isopropyl. In some embodiments, Z is selected from hydrogen and methyl.

In exemplary embodiments, the aromatic polymer may be selected from Formulas (IV)-(IX).

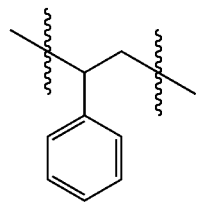

(IV)

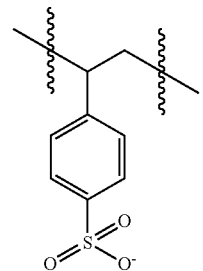

(V)

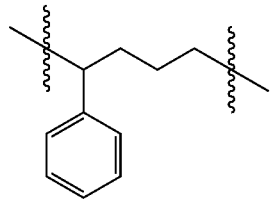

(VI)

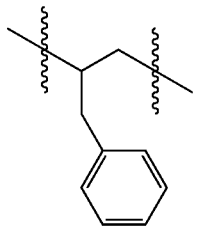

(VII)

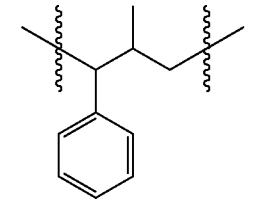

(VIII)

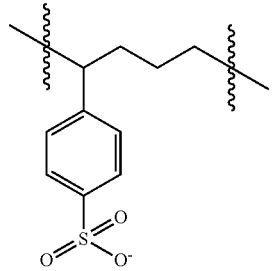

(IX)

In some embodiments, the aromatic polymer is electrospun polystyrene (i.e. wherein at least one pyrene is not covalently bound to the polystyrene).

As used herein, the term "small molecule," when used in reference to the fluorophore, denotes a compound that is not covalently bound to a polymer and not itself the product of polymerization, gene transcription or translation (e.g. polymer, protein, RNA, or DNA) and has a low molecular weight (e.g. molecules having a molecular weight of less than about 2,000 daltons). It is to be understood that the small molecule fluorophores of the present teachings are not covalently bound to the aromatic polymer in the explosive detection substrate. In some embodiments, small molecules have a molecular weight of less than about 1,500 Da. In other embodiments, small molecules have a molecular weight of less than about 1,000 Da. In still other embodiments, small molecules have a molecular weight of less than about 750 Da. In yet other embodiments, small molecules have a molecular weight of less than about 500 Da.

Although the small molecule fluorophore is not limited to macrocyclic compounds, in some embodiments, the small molecule fluorophore is an aromatic multi-ring hydrocarbon and/or an aromatic multi-ring heterocycle, either of which may be optionally substituted. In some embodiments, the term "multi-ring" refers to a compound having 3-5 fused ring structures (such as anthracene, naphthofuran, perylene or pyrene). Conjugation of electrons in these aromatic systems results in a low energy π* lowest unoccupied molecular orbital and a low energy delocalized excited state. Thus, such conjugated compounds are electron donors and may be used for redox sensing of electron-deficient analytes, such as nitrogen-based explosives, through electron-transfer luminescence quenching. In some embodiments, the small molecule fluorophore is an aromatic four-ring hydrocarbon or an aromatic four-ring heterocycle, which may be optionally substituted. In some embodiments, the aromatic multi-ring hydrocarbon or the aromatic multi-ring heterocycle is substituted with an electron donating group. Electron donating groups are known to those of skill in the art.

For example, in some embodiments, the small molecule fluorophore includes compounds of Formula (II) or Formula (III):

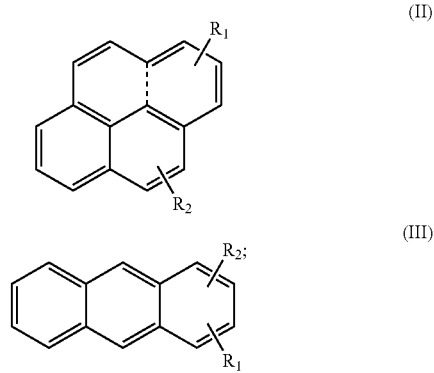

wherein $R_1$ and $R_2$ are each independently selected from hydrogen, cyano, alkyl, —B(OH)$_2$, —C(O)H, -alkyl-C(O)H, —C(O)-alkyl, -alkyl-C(O)-alkyl, —C(O)OH, -alkyl-C(O)OH, —C(O)O-alkyl, -alkyl-C(O)O-alkyl, —C(O)O-succinimide and -alkyl-C(O)O-succinimide. In some embodiments, $R_1$ and $R_2$ are each independently selected from hydrogen, cyano, $C_{1-4}$ alkyl, —B(OH)$_2$, —C(O)H, —$C_{1-4}$ alkyl-C(O)H, —C(O)—$C_{1-4}$ alkyl, —$C_{1-4}$ alkyl-C(O)—$C_{1-4}$ alkyl, —C(O)OH, —$C_{1-4}$ alkyl-C(O)OH, —C(O)O—$C_{1-4}$ alkyl, —$C_{1-4}$ alkyl-C(O)O—$C_{1-4}$ alkyl, —C(O)O-succinimide and —$C_{1-4}$ alkyl-C(O)O-succinimide. In some embodiments, $R_1$ and $R_2$ are each independently selected from hydrogen, cyano, methyl, ethyl, propyl, —B(OH)$_2$, —C(O)H, —$C_{1-4}$ alkyl-C(O)H, —C(O)CH$_3$, —$C_{1-4}$ alkyl-C(O)CH$_3$, —C(O)OH, —$C_{1-4}$ alkyl-C(O)OH, —C(O)OCH$_3$, —$C_{1-4}$ alkyl-C(O)OCH$_3$, —$C_{1-4}$ alkyl-C(O)O-succinimide. In some embodiments, $R_1$ and $R_2$ are each independently hydrogen.

In some embodiments, the small molecule fluorophore includes pyrene, 1-pyrenebutyric acid, pyrene-1-boronic acid, 1-pyrenebutyric acid N-hydroxysuccinimide ester, and/or mixtures thereof. In certain embodiments, the small molecule fluorophore is pyrene. In some embodiments, the substrate comprises an electrospun polystyrene-pyrene matrix.

In some embodiments, the small molecule fluorophore includes anthracene. In certain embodiments, the substrate comprises an electrospray polystyrene-anthracene matrix.

In some embodiments, properties of the compounds may be tuned using particular substituents in order to produce a desired emission wavelength. Those skilled in the art would recognize which types of functional groups would afford this tuning ability. For example, electron-poor groups, such as acyl, carboxyl, cyano, nitro, sulfonate, or the like, may provide fluorescence emission at shorter wavelengths, whereas electron-rich groups, such as amino, hydroxy, alkoxy (e.g. methoxy), acylamino, acyloxy, alkyl, halide, and the like, may provide fluorescence emission at longer wavelengths.

In some embodiments, the small molecule fluorophore is substantially evenly distributed throughout the substrate. Even distribution may be advantageous (e.g. in providing highly uniform fluorescence throughout the substrate). However, it is to be understood that even distribution is not necessary for proper function of the highly sensitive explosives detection substrates described herein. As used herein, the phrase "substantially evenly distributed" refers to a distribution of particles such that the amount of particles differs less than about 5% between any two distinct portions of the substrate. In some embodiments, the amount of fluorophore particles differs less than about 4% between any two distinct portions of the substrate. In some embodiments, the amount of fluorophore particles differs less than about 3% between any two distinct portions of the substrate. In some embodiments, the amount of fluorophore particles differs less than about 2%, less than about 1%, less than about 0.5%, or even less than about 0.1% between any two distinct portions of the substrate.

In some embodiments, the small molecule fluorophore (e.g. the pyrene) is present in the substrate at about 1% to about 60%, by weight. It is to be understood that too much or too little fluorophore may, depending upon the fluorophore itself, change the amount and nature of π-π interactions, and thus potentially the sensitivity of the substrate. Accordingly, in some embodiments, the small molecule fluorophore is present in the substrate at about 2% to about 55%, by weight. In some embodiments, the small molecule fluorophore is present in the substrate at about 5% to about 45%, by weight. In some embodiments, the small molecule fluorophore is present in the substrate at about 10% to about 35%, by weight. In some embodiments, the small molecule fluorophore is present in the substrate at about 15% to about 25%, by weight. In some embodiments, the small molecule fluorophore is present in the substrate at about 20% by weight.

In some embodiments, the present teachings provide substrates which are highly porous. As used herein, "highly porous" refers to a porosity of at least about 5%. The term porosity is used to denote the ratio of the volume of all the pores (e.g. hollow spaces) in the material to the volume of the whole thereof. Accordingly, the ratio of the open hollow spaces is specified in percent (%) with respect to the external volume, which would correspond to 100%. In some embodiments, the porosity of the substrate is in a range of between about 5% and about 90%, for example between about 10% and about 80%. In some embodiments, the porosity of the substrate is in a range of between about 20% and about 65%. In some embodiments, the porosity of the substrate is in a range of between about 20% and about 55%. In some embodiments, the porosity of the substrate is in a range of between about 20% and about 45%. In some embodiments, the porosity of the substrate is in a range of between about 20% and about 35%. In some embodiments, the porosity of the substrate is in a range of between about 30% and about 65%. In some embodiments, the porosity of the substrate is in a range of between about 30% and about 55%. In some embodiments, the porosity of the substrate is in a range of between about 30% and about 45%. In some embodiments, the substrate is non-woven. Without wishing to be bound by any particular theory, it is believed that a high porosity may be advantageous in allowing the analyte to permeate the material and maximize contact with the fluorophore. It is to be understood, however, that a material with low porosity and/or low surface area (e.g. certain films) will also allow proper function of the explosives detection substrates described herein.

In some embodiments, the present teachings provide substrates which exhibit a high surface to volume ratio. As used herein, "surface to volume ratio" refers to the ratio of the total surface area of the measured sample relative to the total volume of void space in the measured sample. In some embodiments, the surface to volume ratio is expressed in units of $mm^2/mm^3$. In some embodiments, surface to volume ratio may be measured using 3-dimensional topography analysis, which is described, for example, in *Advanced Techniques for Assessment Surface Topography: Development of a Basis for 3D Surface Textures Standards*, Blunt, L et al. (ed.), London: Kogan Page Publishers, 2003. Alternatively, surface to volume ratio may be measured using nuclear magnetic resonance, for example, as described in Butler, J P et al. *Measuring surface-area-to-volume ratios in soft porous materials using laser-polarized xenon interphase exchange nuclear magnetic resonance*, J. Phys.: Condens. Matter 14 (2002) L297-L304 or BET method. In some embodiments, the surface to volume ratio is at least about 1 $mm^2/mm^3$. In some embodiments, the surface to volume ratio is at least about 5 $mm^2/mm^3$. In some embodiments, the surface to volume ratio is at least about 10 $mm^2/mm^3$. In some embodiments, the surface to volume ratio is at least about 25 $mm^2/mm^3$. In some embodiments, the surface to volume ratio is at least about 50 $mm^2/mm^3$. In some embodiments, the surface to volume ratio is at least about 75 $mm^2/mm^3$. In some embodiments, the surface to volume ratio is at least about 100 $mm^2/mm^3$. In some embodiments, the surface to volume ratio is at least about 1000 $mm^2/mm^3$. In some embodiments, the surface to volume ratio is between about 1 $mm^2/mm^3$ and about 10,000 $mm^2/mm^3$.

In some embodiments, the present teachings provide a highly sensitive substrate material. Accordingly, in some embodiments, the substrate is capable of detecting an explosive material in very small amounts. In some embodiments, the substrate is capable of detecting the presence of explosive material in a vapor at concentrations as low as about 200 ppb. In some embodiments, the substrate is capable of detecting the presence of explosive material in a vapor at concentrations as low as about 150 ppb. In some embodiments, the substrate is capable of detecting the presence of explosive material in a vapor at concentrations as low as about 100 ppb, as low as about 75 ppb, as low as about 50 ppb, as low as about 25 ppb, as low as about 10 ppb, as low as about 5 ppb, as low as about 1 ppb, as low as about 0.5 ppb, as low as about 0.1 ppb, as low as about 0.01 ppb, or even as low as about 0.001 ppb. In some embodiments, the substrate is capable of detecting the presence of explosive material in a vapor at concentrations as low as about 1 ppt, as low as about 0.5 ppt, as low as about 0.1 ppt, or even as low as about 0.01 ppt. In some embodiments, explosive material in a vapor at concentrations as low as about 25 ppb can be visualized by the naked eye. In some embodiments, explosive material in a vapor at concentrations as low as about 10 ppb can be visualized by the naked eye. In some embodiments, explosive material in a vapor at concentrations as low as about 5 ppb can be visualized by the naked eye.

In some cases, sensitivity is measured by the amount (in weight) of explosive material required to produce fluorescence quenching. In some embodiments, the substrate is capable of producing fluorescence quenching (e.g. directly visible fluorescence quenching) in the presence of an explosive material in an amount less than about 1 µg, less than about 500 ng, less than about 250 ng, less than about 100 ng, less than about 50 ng, or less than about 25 ng. In some embodiments, the substrate is capable of producing fluorescence quenching in the presence of an explosive material in an amount less than about 10 ng. In some embodiments, the substrate is capable of producing fluorescence quenching in the presence of an explosive material in an amount less than about 5 ng. In some embodiments, the substrate is capable of producing fluorescence quenching in the presence of an explosive material in an amount less than about 1 ng, less than about 0.1 ng or less than about 0.01 ng.

In some embodiments, the explosives detection substrates of the present teachings are capable of detecting an explosive material with a moderate to high vapor pressure. Conventional detectors can typically detect (with varying levels of sensitivity) higher vapor pressure explosive materials, because the material is present, at least in part, in the air/atmosphere that has been exposed to the solid material. In some embodiments, the explosives detection substrates of the present teachings are also capable of detecting an explosive material with a low vapor pressure. Detecting low vapor pressure explosive materials is generally difficult, because a solid sample leaves very little trace of the material in the air/atmosphere. As used herein, a material having "low vapor pressure" refers to a material with a vapor pressure of less than about $1 \times 10^{-5}$ Torr at room temperature/atmospheric pressure. As used herein, a material having "moderate to high vapor pressure" refers to a material with a vapor pressure of greater than about $1 \times 10^{-5}$ Torr at room temperature/atmospheric pressure. Vapor pressure can also be denoted by the concentration of particles present in the air/atmosphere around the material. Accordingly, as used herein, "low vapor pressure" material can also refer to a material with a vapor pressure of less than about 10 ppb at room temperature/atmospheric pressure and "moderate to high vapor pressure" material can also refer to a material with a vapor pressure of greater than about 10 ppb at room temperature/atmospheric pressure. In some embodiments, the explosives detection substrates of the present teachings are capable of detecting an explosive material with a vapor pressure of less than about $1 \times 10^{-6}$ Torr at room temperature/atmospheric pressure. In some embodiments, the explosives detection substrates of the present teachings are capable of detecting an explosive material with a vapor pressure of less than about $1 \times 10^{-7}$ Torr at room temperature/atmospheric pressure. In some embodiments, the explosives detection substrates of the present teachings are capable of detecting an explosive material with a vapor pressure of less than about $1 \times 10^{-8}$ Torr, less than about $1 \times 10^{-9}$ Torr, or less than about $1 \times 10^{-10}$ Torr at room temperature/atmospheric pressure. Vapor pressures of certain explosives materials may be found, for example, in Moore, D. S., *Rev. Sci. Instrum.* 75 (8): 2499-2512, 2004 (see, e.g., FIG. 1). Vapor pressures for various analytes and interferences, as well as vapor concentrations and LUMO energies, are provided in FIG. 1. Explosive materials with a low vapor pressure include, but are not limited to, octahydro-1,3,5,7-tetranitro-1,3,5,7-tetrazocine (HMX), hexahydro-1,3,5-trinitro-1,3,5-triazine (RDX), ammonium perchlorate (AP), methyl-2,4,6-trinitrophenylnitramine (Tetryl), picric acid (PA), hexanitrostilbene (HNS) and pentaerythritol tetranitrate (PETN).

In some embodiments, the present teachings provide a substrate material that allows for quick detection of explosive materials. In some embodiments, for example, the substrate is capable of detecting an explosive material in less than about 6 minutes. In some embodiments the substrate is capable of detecting an explosive material in less than about 5 minutes. In some embodiments the substrate is capable of detecting an explosive material in less than about 4 minutes. In some embodiments the substrate is capable of detecting an explosive material in less than about 3 minutes, less than about 2 minutes, less than about 1 minute, less than about 30 seconds, less than about 20 seconds, or less than about 10 seconds. In some embodiments the substrate is capable of detecting an explosive material in less than about 5 seconds. The time of detection can vary within the parameters above, but will generally depend upon the concentration of explosive material exposed to the substrate.

Methods for Explosives Detection

In some embodiments, the present teachings provide methods for detecting an explosive material. The method includes, for example, contacting the explosives detecting substrate as described herein with an explosive material for a given period of time; measuring the amount of fluorescence emitted by the explosives detecting substrate; and comparing the amount of fluorescence with a suitable control. In such methods, an explosive material is detected where the fluorescence of the explosives detecting substrate is less than the fluorescence of the suitable control. In other embodiments, the present teachings provide methods for screening a test sample for the presence of an explosive material. The method includes, for example, contacting the explosives detecting substrate as described herein with the test sample for a given period of time; measuring the amount of fluorescence emitted by the explosives detecting substrate; and comparing the amount of fluorescence with a suitable control. In such methods, the presence of an explosive material is detected in the test sample where the fluorescence of the explosives detecting substrate is less than the fluorescence of the suitable control.

In some embodiments, the present teachings utilize luminescent compounds to detect explosive materials (e.g. nitrogen-based explosives) through luminescence quenching. Direct interaction of an electron-accepting analyte (such as an explosive material) with a small molecule fluorophore in the explosives detecting substrate described herein can cause luminescence quenching. Such quenching can be monitored to identify the presence of explosives. For example, a substrate may be exposed to an environment suspected of being contaminated with explosives and subsequently observed to determine the presence of explosives through luminescence quenching.

In some embodiments, the explosives detecting substrate is contacted with an explosive material (or a test sample) for at least about 6 minutes. In some embodiments, the explosives detecting substrate is contacted with an explosive material (or a test sample) for at least about 30 seconds. In some embodiments, the explosives detecting substrate is contacted with an explosive material for at least about 5 seconds. In some embodiments, the explosives detecting substrate is contacted with an explosive material for at least about 5 minutes, at least about 4 minutes, at least about 3 minutes, at least about 2 minutes, at least about 1 minute, at least about 45 seconds, or at least about 15 seconds. In some embodiments, the explosives detecting substrate is contacted with an explosive material (or a test sample) for less than about 6 minutes, less than about 5 minutes, less than about 4 minutes, less than about 3 minutes, less than about 2 minutes, less than about 1.5 minutes, less than about 60 seconds, less than about 30 seconds, less than about 15 seconds, less than about 10 seconds, or even less than about 5 seconds. In some embodiments, the explosives detecting substrate is contacted with an explosive material (or a test sample) for a time period of between about 1 second and about 6 minutes. The time of exposure will depend upon the concentration of explosive material in the sample (or suspected to be in the sample). For example, a sample may be exposed to the substrate for a longer period of time, but begin to show quenching after only a few seconds. In some embodiments, the explosives detecting substrate is contacted with an explosive material (or a test sample) for about six minutes or until quenching occurs, whichever is greater.

As used herein, the term "suitable control" refers to a control based upon fluorescence levels in an explosives detection substrate that has not been exposed to an explosive material. That is, in some embodiments, the suitable control is a predetermined fluorescence level or value. In some embodiments, the suitable control is a fluorescence level detected from a single explosives detection substrate known to have not been exposed to an explosive material. In some embodiments, the suitable control is an average fluorescence level from a plurality of explosives detection substrates which have not been exposed to an explosive material. In some embodiments, the suitable control is a fluorescence level detected in a portion of the explosives detection substrate that has not been exposed to an explosive material. For example, often detection of an explosive material may be confirmed by visually observing (e.g. under UV light) dark quenched spots amidst the bright background of the explosives detection substrate. In this situation, the bright background would be the suitable control.

In some embodiments, the present teachings provide an explosives detection substrate capable of simultaneously detecting a wide range of explosive materials, such as nitrogen-based explosives, including nitroaromatic-, nitramine- and organic nitrate-based explosives. Many nitrogen-based explosives are electron-acceptors. In nitroaromatics, for example, the $\pi^*$ lowest unoccupied molecular orbitals (LUMOs) are of low energy due to the electron-withdrawing effect of the nitro substituent on the aromatic ring. A higher degree of nitro-substitution results in a higher reduction potential and a greater oxidizing ability (nitrobenzene (−1.15 V), dinitrotoluene (−0.9 V), and trinitrotoluene (−0.7 V), versus normal hydrogen electrode (NHE)). Similarly, organic molecules functionalized with nitro groups have lower energy LUMOs, which increase their oxidizing abilities. Thus, organic nitro compounds, such as the nitramine explosives (e.g. RDX) and the organic nitrates (e.g. PETN and nitroglycerin), have increased electron-accepting abilities compared to certain other organic compounds.

In some embodiments, the methods of the present teachings detect an explosive material with a moderate to high vapor pressure. In some embodiments, the methods of the present teachings detect an explosive material with a low vapor pressure. In some embodiments, the methods of the present teachings detect an explosive material with a vapor pressure of less than about $1\times10^{-6}$ Torr at room temperature/atmospheric pressure. In some embodiments, the methods of the present teachings detect an explosive material with a vapor pressure of less than about 1×10⁻⁷ Torr at room temperature/atmospheric pressure. In some embodiments, the methods of the present teachings detect an explosive material with a vapor pressure of less than about $1\times10^{-8}$ Torr, less than about $1\times10^{-9}$ Torr, or less than about $1\times10^{-10}$ Torr at room temperature/atmospheric pressure.

In some embodiments, the methods of the present teachings are capable of detecting an explosive listed in Bureau of Alcohol, Tobacco and Firearms *Commerce in Explosives; List of Explosive Materials* (2010R-27T), Federal Register, Vol. 75, No. 221, P 70291, 2010. In some embodiments, the present teachings provide an explosives detection substrate capable of detecting explosive materials, including, but are not limited to octahydro-1,3,5,7-tetranitro-1,3,5,7-tetrazocine (HMX), hexahydro-1,3,5-trinitro-1,3,5-triazine (RDX), 1,3,5-trinitrobenzene (TNB), 1,3-dinitrobenzene (DNB), methyl-2,4,6-trinitrophenylnitramine (Tetryl), nitrobenzene (NB), 2,4,6-trinitrotoluene (TNT), picric acid (PA), ammonium perchlorate (AP), 2,4-dinitrotoluene (24DNT), 2,6-dinitrotoluene (26DNT), o-nitrotoluene (2NT), m-nitrotoluene (3NT), p-nitrotoluene (4NT), nitroglycerin (NG), 4-amino-2,6-dinitrotoluene (4-Am-DNT), 2-amino-4,6-dinitrotoluene (2-Am-DNT), pentaerythritol tetranitrate (PETN), 2,3-dimethyl-2,3-dinitrobutane (DMNB), hexanitrostilbene (HNS), nitroamines, nitroamides, nitroesters, other nitro- or nitrate-containing species, and the like. Explosive molecules are generally semi-volatile organic compounds and the presence of the above compounds can indicate the presence of explosives or munitions, such as landmines or unexploded ordnance (UXO) (e.g. in a sample or in the soil subsurface).

In some embodiments, the present teachings provide methods of detecting Tetryl in a sample suspected of containing an explosive material. In some embodiments, the present teachings provide methods of detecting RDX in a sample suspected of containing an explosive material. In some embodiments, the present teachings provide methods of detecting 24DNT in a sample suspected of containing an explosive material. In some embodiments, the present teachings provide methods of detecting PETN in a sample suspected of containing an explosive material.

In some embodiments, the methods of the present teachings detect an explosive material in very small amounts. In some embodiments, the methods of the present teachings detect the presence of explosive material in a vapor at concentrations as low as about 200 ppb, as low as about 150 ppb, as low as about 100 ppb, as low as about 90 ppb, as low as about 80 ppb, as low as about 70 ppb, as low as about 60 ppb, as low as about 50 ppb, as low as about 40 ppb, as low as about 30 ppb, as low as about 20 ppb, as low as about 10 ppb, as low as about 5 ppb, as low as about 1 ppb, as low as about 0.5 ppb, as low as about 0.1 ppb, as low as about 0.01 ppb, or even as low as about 0.001 ppb. In some embodiments, the methods of the present teachings detect the presence of explosive material in a vapor at concentrations as low as about 1 ppt, as low as about 0.5 ppt, as low as about 0.1 ppt, or even as low as about 0.01 ppt. In some embodiments, explosive material in a vapor at concentrations as low as about 25 ppb can be visualized by the naked eye. In some embodiments, fluorescence quenching resulting from the presence of explosive material in a vapor at concentrations as low as about 10 ppb can be visualized by the naked eye (e.g. when material is illuminated with UV light). In some embodiments, fluorescence quenching resulting from the presence of explosive material in a vapor at concentrations as low as about 5 ppb can be visualized by the naked eye (e.g. when material is illuminated with UV light). In some embodiments, the methods of the present teachings are capable of detecting an explosive material in an amount less than about 10 ng. In some embodiments, the methods of the present teachings are capable of detecting an explosive material in an amount less than about 1 ng.

In some embodiments, such as where the fluorophore is luminescent in the visible spectrum, the quenching may be observed through either direct or indirect visual examination. In some embodiments, the substrate is placed in a dark environment and exposed to a wavelength of light capable of exciting luminescence from the reagent. The excitation source utilized may be, for example, a black light, a blue light, a white light, a UV lamp, a mercury-deuterium lamp, xenon-arc lamp, light emitting diodes, or cathode ray tubes. The excitation source or light source can be chosen to maximize excitation of the luminescent compound while simultaneously minimizing the degree of photodegradation. In some embodiments, quenching may be observed through indirect visual examination using a camera or other instrumentation as an intermediary. Additionally or alternatively, the quenching may be recorded with the use of a visible or ultra-violet camera, or with the use of a fluorimeter or fluorescence spectrometer. The instrumentally recorded data may be analyzed directly or by using computer software to interpret results and make a determination of whether or not explosives are present.

In some embodiments, the quenching may be observed as a change in the emission of the explosives detection substrate, for example a change in the wavelength of the luminescence emission. Accordingly, in some embodiments, methods of the present teachings can include determining a change in the wavelength of the luminescence emission. Methods for determining changes in wavelength are known in the art.

In some embodiments, detection can occur without the use of heat. In other embodiments, however, the substrate can be exposed to heat and/or forced air flow after contact with the environment suspected of being contaminated by explosives. Heat exposure can speed the evaporation of solvent and/or increase the rate of interaction between the explosive material and the substrate. In some embodiments, detection can occur at a temperature of about 0° C. to about 100° C.

The methods of the present teachings allow for the detection of explosive materials in a number of environments, including in the air and on surfaces such as hands, clothing, cars, packages, luggage, door handles, buildings, land, desks, computers, and more.

Methods for Forming Substrates

In some embodiments, the present teachings provide methods for forming an explosives detecting substrate. The method includes electrospinning an aromatic polymer in the presence of a small molecule fluorophore such that an explosives detecting substrate is formed. Although electrospinning may provide certain advantages (e.g. a highly porous nonwoven structure) it is to be understood that the explosives detection materials described herein can also be produced by other methods known in the art (e.g. film extrusion, film casting or electrospraying).

Electrospinning uses an electrical charge to draw fine (e.g. micro or nano scale) fibers from a liquid. When a sufficiently high voltage is applied to a liquid droplet, the liquid body develops a charge. Electrostatic repulsion counteracts the surface tension and the droplet of liquid is stretched from the surface of the apparatus. A stream of liquid is then discharged from the surface at a point called the Taylor cone. When molecular cohesion of the liquid is sufficiently high, the stream remains intact. This is in contrast to electrospraying, where the stream does not remain intact. The jet elongates due to electrostatic repulsion initiated at small bends in the fiber, until the fiber is deposited on a grounded collector.

Laboratory equipment for electrospinning can include, for example, a spinneret (e.g. a syringe needle) connected to a high-voltage (5 to 50 kV) direct current power supply, a syringe pump, and a grounded collector. A polymer solution, sol-gel, particulate suspension or melt is loaded into the syringe and this liquid is extruded from the needle tip at a constant rate (e.g. by a syringe pump).

In some embodiments, parameters of the electrospinning process may affect the resultant substrate (e.g. the thickness, porosity, etc.). Such parameters may include, for example, molecular weight, molecular weight distribution and architecture (branched, linear etc.) of the polymer, solution properties (viscosity, conductivity & and surface tension), electric potential, flow rate, concentration, distance between the capillary and collection screen, ambient parameters (temperature, humidity and air velocity in the chamber) and the motion of the grounded collector. Accordingly, in some embodiments, the method of producing a substrate as described herein includes adjusting one or more of these parameters.

The conductivity of the electrospinning solution may affect the morphology of the resultant electrospun fibers. Without wishing to be bound by any particular theory, it is believed that higher conductivity typically results in nanofibers exhibiting better morphology.

The conductivity of the electrospinning solution may adjusted by the addition of an additive, such as an organic salt. In some embodiments, the additive may be selected from the group consisting of organic salts, or mixtures thereof. The additive may be selected from the group consisting of tetrabutylammonium hexafluorophosphate (TBAP), sodium 1-heptene-2-sulfonate, ammonium bromide, 1-naphthyl phosphate calcium salt trihydrate, ammonium hexafluorophosphate, tetramethylammonium hexafluorophosphate, and tetrabutylammonium hydroxide 30-hydrate.

In some embodiments, the diameter of fibers resulting from electrospinning the aromatic polymer in the presence of a small molecule fluorophore is less than about 200 nm or even less than about 150 nm. In some embodiments, the diameter of fibers resulting from electrospinning aromatic polymer in the presence of a small molecule fluorophore is between about 50 nm and about 150 nm. In some embodiments, the diameter of fibers resulting from electrospinning aromatic polymer in the presence of a small molecule fluorophore is between about 100 nm and about 125 nm.

In some embodiments, the thickness of the substrate can be controlled by the electrospinning time. Generally, the efficiency of the substrates described herein is not affected by the thickness of the substrate. Typically, with conventional films, a film that is too thick may create excess luminescence, such that quenching will not be observed or will be difficult to observe, whereas a film that is too thin may show inadequate detection due to low emission intensity. However, possibly due to the favorable porosity of the explosives detection substrate described herein, the thickness does not appear to drastically affect the luminescence or quenching. Accordingly, in some embodiments, the thickness of the substrate is between about 100 nm and about 100 µm. In some embodiments, the thickness of the substrate is between about 200 nm and about 10 µm. In some embodiments, the thickness of the substrate is less than about 1 µm.

In some embodiments, the substrate is electrospun directly onto the area to be tested (e.g. land suspected of containing landmines). Therefore, fluorescence quenching can be observed using a handheld UV light, thus identifying explosive materials such as vapor or landmines. In some embodiments, the substrate can be mass produced as rolls. The substrate can then be un-rolled over the area to be tested (e.g. large land areas suspected of having buried landmines). In some embodiments, the substrate is formed directly on surfaces to be tested, such as hands, clothing, cars, packages, luggage, door handles, buildings, land, desks, computers, and more.

Other methods known in the art to produce porous substrates, such as dry spinning or (electro)spraying, may be used to for the explosives detecting substrates described herein.

Sensors and/or Kits for Explosive Detection

In some embodiments, the present teachings provide sensors and/or kits for explosives detection. In some embodiments, the sensors and/or kits include the explosives detecting substrate described herein. A "sensor" refers to any device or article capable of detecting an explosive material.

In some embodiments, the kits include an aromatic polymer and a small molecule fluorophore, packaged with instructions for forming an explosives detecting substrate. In some embodiments, the kit further includes equipment for electrospinning the aromatic polymer in the presence of the small molecule fluorophore. In some embodiments, the kit further includes a UV light (e.g. a handheld UV light) and/or instructions for detecting an explosive material.

The sensor may further comprise other common features of explosives detectors, for example, an emission detector positioned to detect fluorescence emission (or lack thereof); an inlet for intake of a sample (e.g. vapor sample, solution sample); and/or a sample cell constructed and arranged to receive the sample. In some embodiments, the sensor includes a complementary analytical device (e.g. a device which performs fluorimetry, absorption spectroscopy, mass spectroscopy, Raman, and/or other appropriate analytical technique). Such analytical devices, when utilized with the explosives detection substrate of the present teachings, can increase the sensitivity of a sensor. In some embodiments, the sensor includes a fluorimeter. The use of a fluorimeter in conjunction with the explosives detection substrate of the present teachings may increase the sensitivity of a sensor by allowing the detection of very small changes is fluorescence intensity (e.g. changes that may not be noticeable upon direct visual inspection). The use of a fluorimeter in conjunction with the explosives detection substrate of the present teachings may also decrease the time required to detect the presence of an explosive material. For example, it may take a few minutes to visually inspect a substrate for quenching, whereas the use of a sensor (e.g. with a fluorimeter) may only require a few seconds. In some embodiments, the sensor includes an absorption spectrometer. In some embodiments, the sensor includes a mass spectrometer.

In one embodiment, the sensor also includes an article to provide enhanced rigidity, sensitivity, selectivity, stability, or a combination of any number of these features, to the explosives detection substrate in the sensor. The article can be positioned adjacent the substrate and can be selected from beads, nanoparticles, polymer fibers, waveguides and a film. In one embodiment, a sensor can be provided comprising an explosives detection substrate positioned adjacent to a waveguide. Light emitted by the explosives detection substrate in one area can be captured by internal reflection in the substrate and then reabsorbed and re-emitted in a different region of the sensor. This process can occur many times before reaching a detector, resulting in a sensor with enhanced sensitivity. Sequential emission and reabsorption cycles increase the probability that an excitation will be quenched or trapped by an analyte.

In some embodiments, the kit and/or sensor is a robot or a remote controlled device. For example, in some embodiments, the explosives detection substrate, or optionally the electrospinning system can be incorporated into a remote controlled vehicle, such as an unmanned vehicle or aircraft. In the latter case, in-situ electrospinning of the explosives detection substrate over large land can be achieved. Placing the explosives detection substrate, or optionally the electrospinning system, into a non-human system can result in fast screening of test environments in large scale with little or no danger to humans.

EXEMPLIFICATION

The embodiments of the present teachings can be understood further by the following examples. It will be appreciated, however, that these examples do not limit the present teachings. Variations of the present teachings, now known or further developed, are considered to fall within the scope of the present teachings as described herein and as hereinafter claimed.

Example 1

Preparation and Characterization of an Electrospun Pyrene/PS Membrane

An exemplary explosive detection substrate was fabricated by electrospinning a mixed solution of pyrene with a supporting matrix of polystyrene (PS). Briefly, a solution was prepared containing 0.1 M pyrene, 4 wt % PS and 5 wt % tetrabutylammonium hexafluorophosphate (TBAP). The solution was electrospun using a 23 gauge needle with a flow rate of 0.8 mL/hr at an applied potential of 23 kV and a collection distance of 10 cm. The collection time was 10 min. The nanofibers can be electrospun on a variety of substrates, including aluminum foil, glass, and filter paper. The composition of the final substrate was 18.4 wt % pyrene, 36.3 wt % PS and 45.3 wt % TBAP.

Electrospinning pyrene with PS generates a uniform fluorescent membrane with a well-defined nanostructure, as shown in FIG. 2. The electrospun membrane presents a non-woven format under a bright-field microscope (FIGS. 2A and 2D). When excited with UV light under a fluorescence microscope, a strong green fluorescent emission was observed from the electrospun pyrene/PS membrane (FIG. 2B), whereas the control electrospun PS membrane did not show any fluorescence under the same excitation (FIG. 2D). Moreover, the green fluorescence was homogeneous within the entire nanofibrous membrane, indicating an even distribution of pyrene in the electrospun membrane. The detailed morphology was further investigated by SEM in FIG. 2C. The electrospun membrane presents a highly porous 3-dimensional mesh structure and consisted of numerous randomly-oriented nanofibers with a relatively uniform diameter of about 100 nm. The morphology of pyrene immobilized electrospun nanofibers was similar to that of PS nanofibers (FIG. 2F), but with a slightly larger diameter. Without wishing to be bound by any particular theory, it is believed that such nanofibrous mesh structure creates a large surface-to-volume ratio and a high porosity, which in turn minimizes the analyte vapor diffusion resistance and provides access to the pyrene.

Figure 3A:
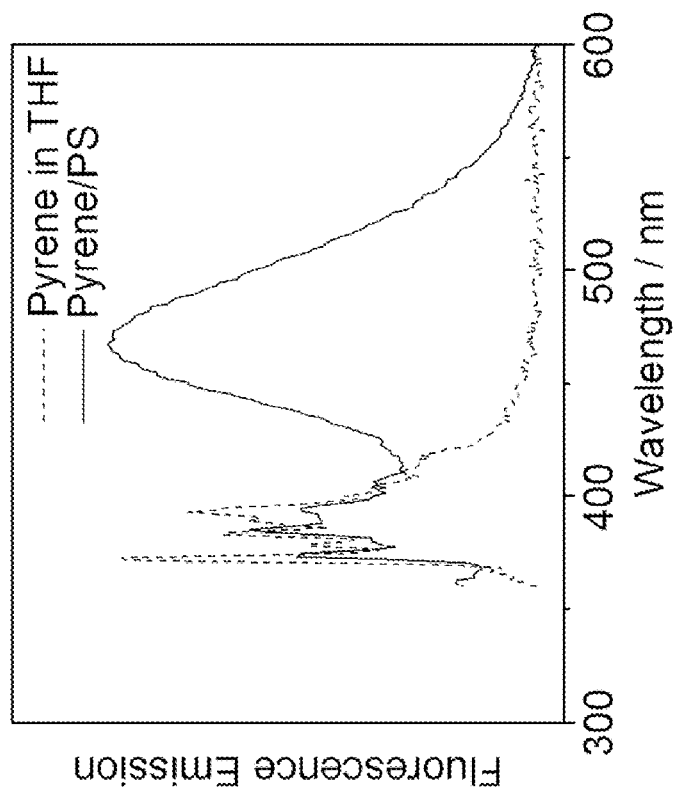
FIGS. 3A and 3B are graphs showing the absorbance and emission spectra of an exemplary electrospun pyrene/PS substrate of the present teachings and 0.1 M pyrene in THF solution.
Figure 3B:
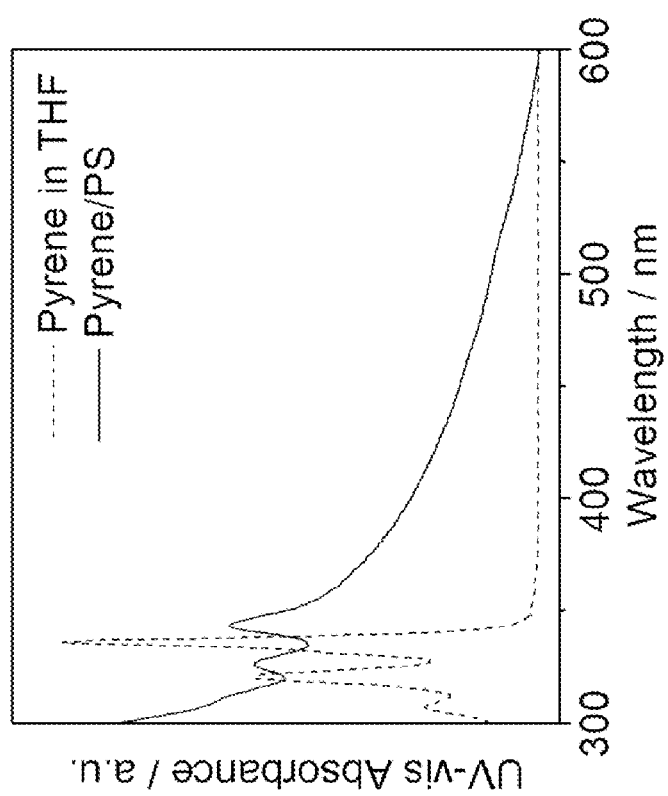

It was postulated that photophysical behavior of the electrospun PS/fluorophore should be very different from that of the fluorophore in the free state, due to the restrictions from the surrounding template. FIG. 3 depicts the steady-state UV-vis absorption and fluorescence emission spectra of electrospun pyrene/PS nanofibers, along with those of pyrene mixed with PS in a THF solution. The absorption spectrum of pyrene in solution shows three well-defined absorption bands at 307, 320 and 336 nm, corresponding to the three vibrational sub-bands of the pyrene ring (S0→2, while S0→S1 is very weak at 375 nm). When the same amount of pyrene was electrospun with PS, the nanofibers exhibit two strong visible peaks at 326 nm and 343 nm and a weak absorption shoulder at 312 nm. Without wishing to be bound by any particular theory, it is believed that the red shift among absorbance peaks (~6 nm) may be attributed to the extended π-π stacking of the aromatic electrons between pyrene rings and phenyl units of PS chain.

Additional characteristics are revealed from the fluorescence emission spectra of the pyrene/PS nanofibers and pyrene in THF solution, also shown in FIG. 3. As a well-studied fluorophore, pyrene has a typical emission range in the near UV region due to the emission from the singlet excited pyrene monomers, which is reflected in the fine structured emission bands of pyrene in THF solution. However, the emission of electrospun pyrene/PS nanofibers is composed of two bands, the first consistent with a pyrene monomer at below 400 nm range, and a dominant broad peak centered at about 468 nm, which may be ascribed to π-π stacking of the pyrene. Many researchers investigating pyrene and its derivatives claim such a peak is due to the formation of pyrene excited dimers, or "excimers". However, in the present case, such π-π stacking may also come from the interaction between phenyl groups of the PS side chains and the planar pyrene rings.

Absorption and emission spectra of exemplary substrates with varying pyrene concentrations have also been investigated. As shown in FIG. 4A, the adsorption peaks appear at 340 and 324 nm for the electrospun nanofibers containing 18.4 wt % pyrene, and 312, 326, 342 nm when increasing the pyrene content to 18.4 wt %. The larger red-shift with higher pyrene content may be a consequence of the extended π-π stacking. For a higher pyrene content (52.9 wt %), however, the adsorption peaks below 350 nm diminish, while a broad yet obvious peak emerges at about 373 nm. This may be due to the vibrational sub-band of single electron transfer of pyrene ring (S0→S1) and is normally very weak for dilute or moderate pyrene concentrations. Additional features are revealed from fluorescence emission in FIG. 4B. Blank PS nanofibers are non-fluorescent, and substrates having dilute pyrene content (2.2 wt %) only show emission peaks below 400 nm, which are identical to those of pyrene in THF solution. Accordingly, it is postulated that these solutions may not take full advantage of favorable π-π stacking. The emission peak at 468 nm appears and becomes dominant when pyrene content is increased to 18.4 wt %, suggesting that the stacking occurs favorably in moderate amounts of pyrene. It is to be noted that the emission at 468 nm is much longer than that of the pyrene monomer with characteristic peaks less than 400 nm, and such visible shining blue luminescence is favorable when direct visual detection is utilized.

Example 2

Fluorescence Quenching with DNT Vapor

Figure 5A:
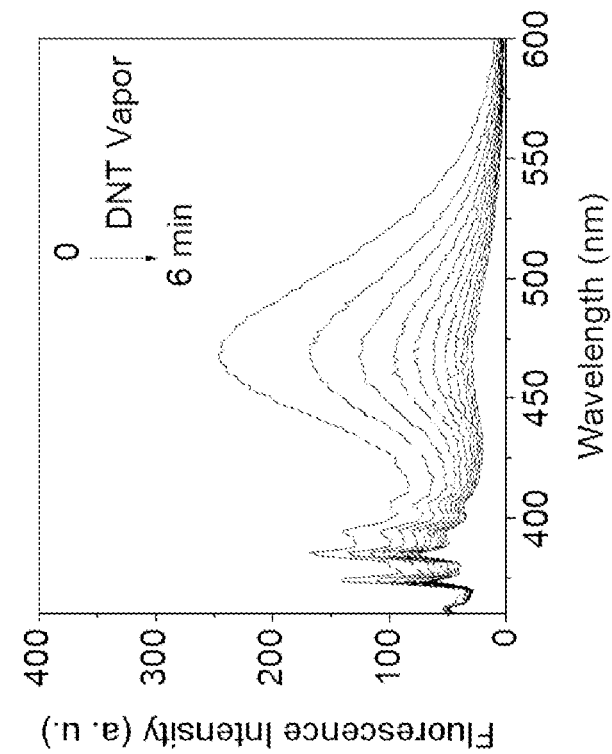
FIGS. 5A-C are fluorescence spectra showing the change in intensity of electrospun pyrene/PS nanofibrous membrane with a pyrene content 2.2 wt % (A), 18.4 wt % (B), and 52.9 wt % (C) as a function of saturated DNT vapor exposure time (0-6.0 min, from top to bottom).
Figure 5B:
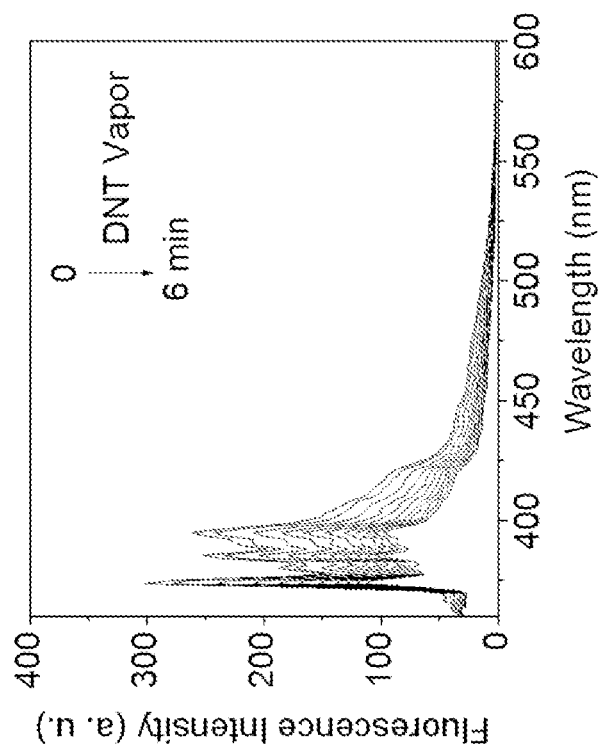
Figure 5C:
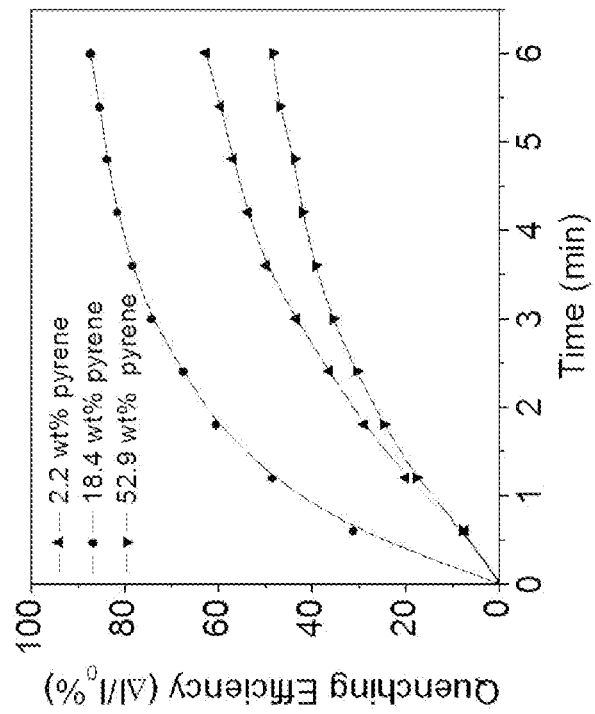
Figure 5D:
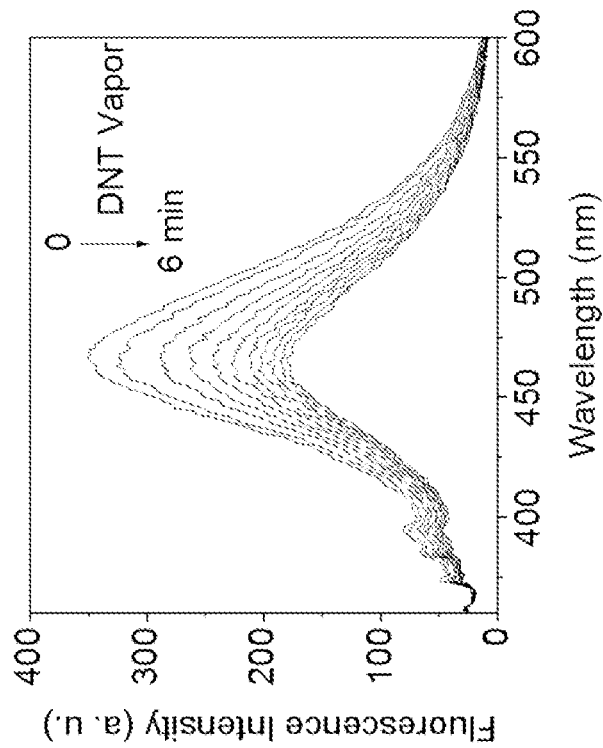
FIG. 5D is the time-dependent fluorescence quenching efficiency of the above substrates.
Figure 6A:
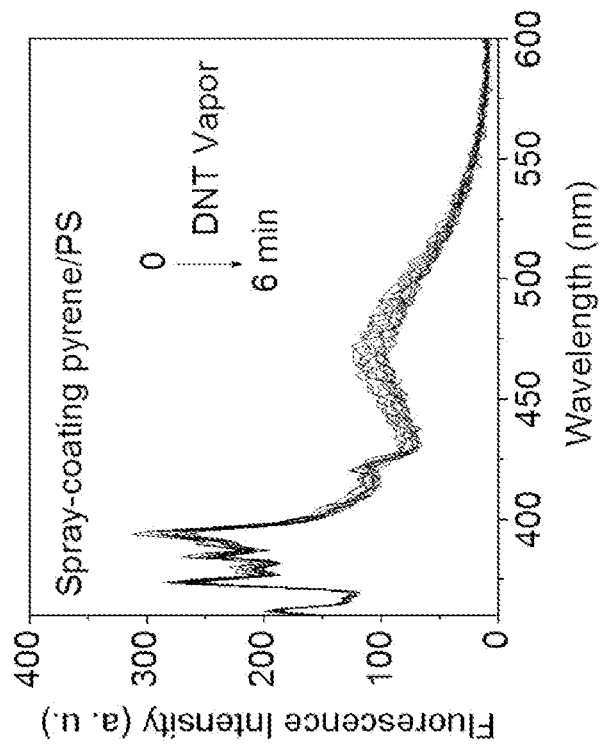
FIGS. 6A-C are fluorescence spectra of dip-coating (A), spray-coating (B), spin-casting (C) pyrene/PS membrane (pyrene content 18.4%) upon exposure to saturated DNT vapor (100 ppb).
Figure 6B:
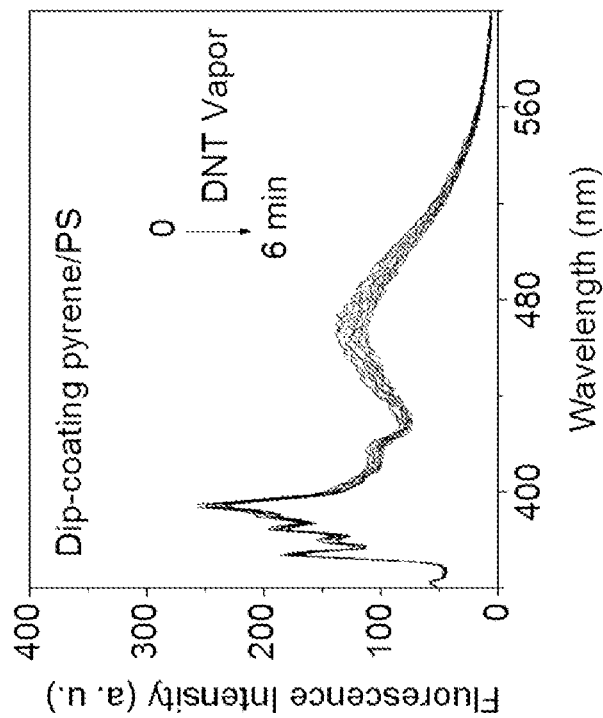
Figure 6D:
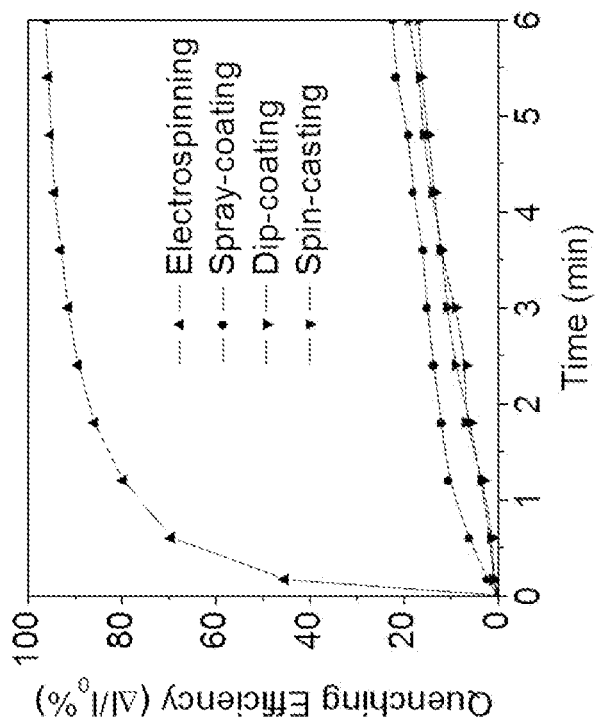
FIG. 6D is the time-dependent fluorescence quenching efficiency of the above substrates.
Figure 6C:
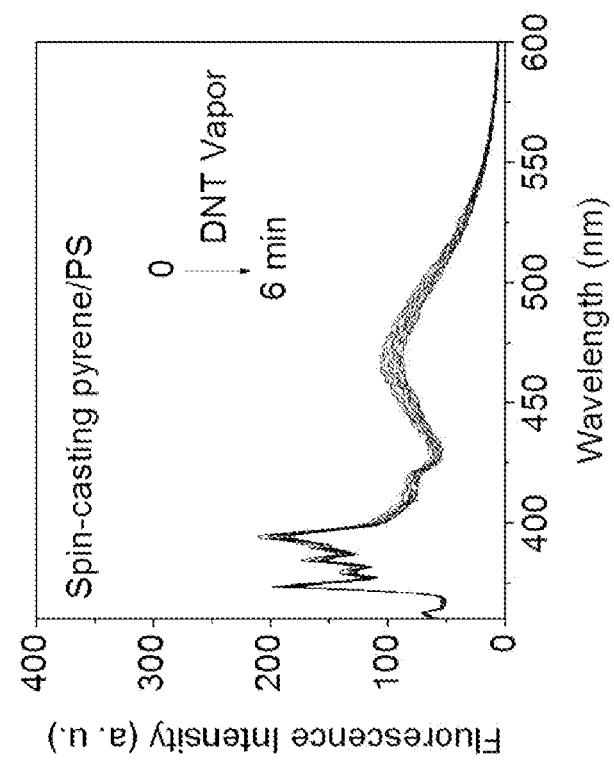
Figure 7A:
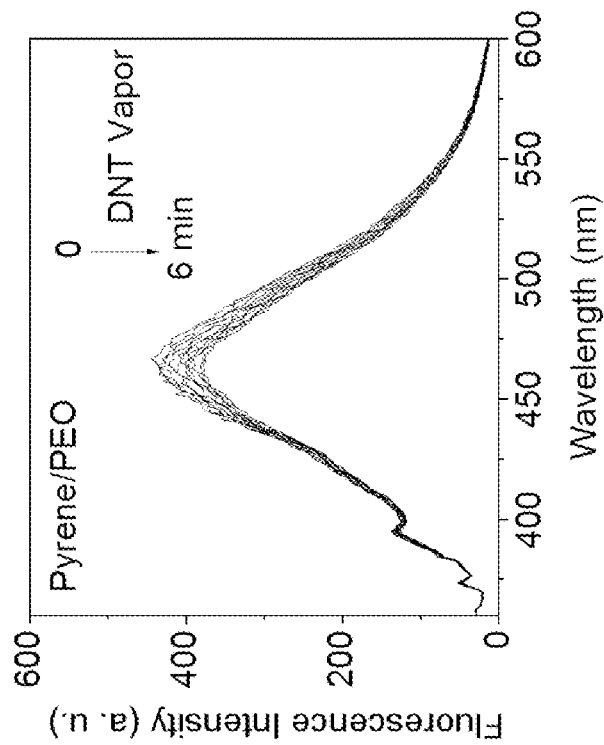
FIGS. 7A-D are fluorescence spectra of electrospun pyrene with PAN (A), PEO (B), PVP (C), and Nylon 6 (D) upon exposure to saturated DNT vapor (100 ppb).
Figure 7B:
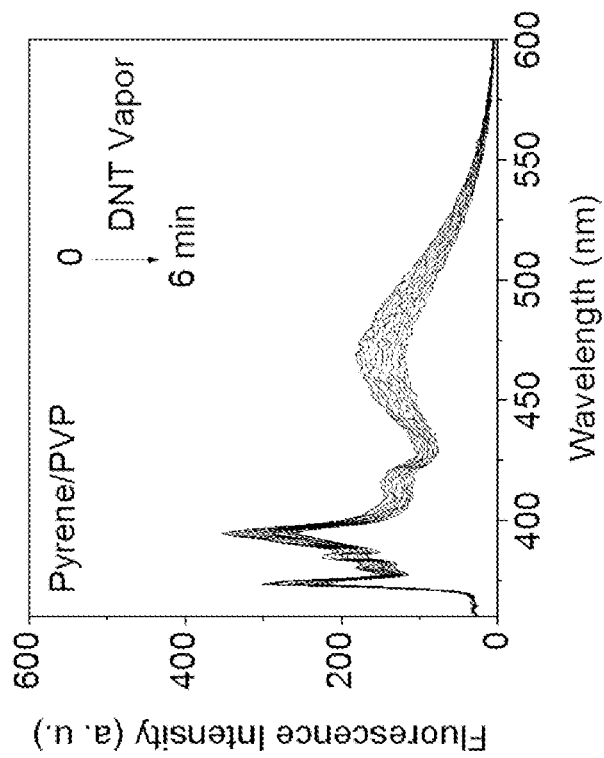
Figure 7D:
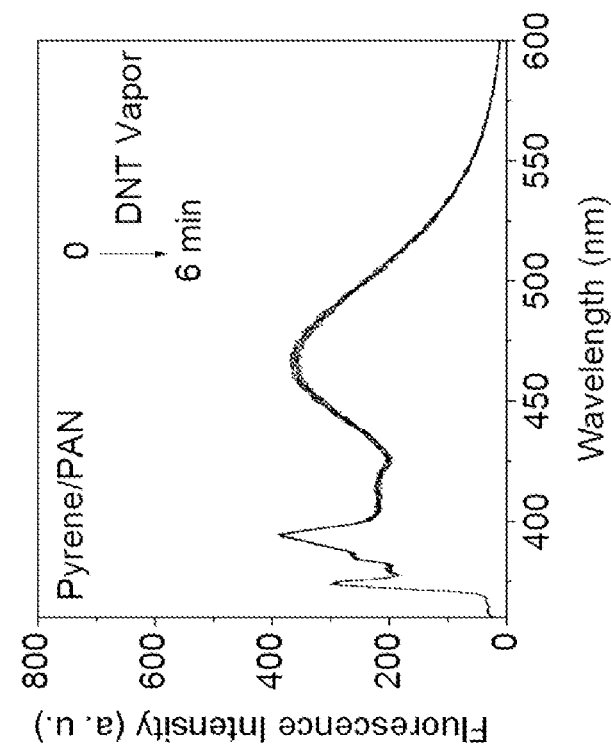
Figure 7C:
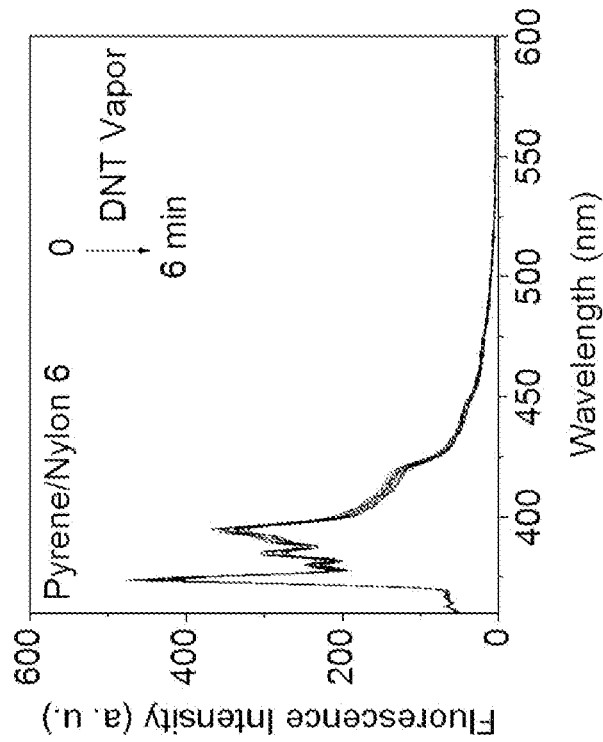
Figure 7E:
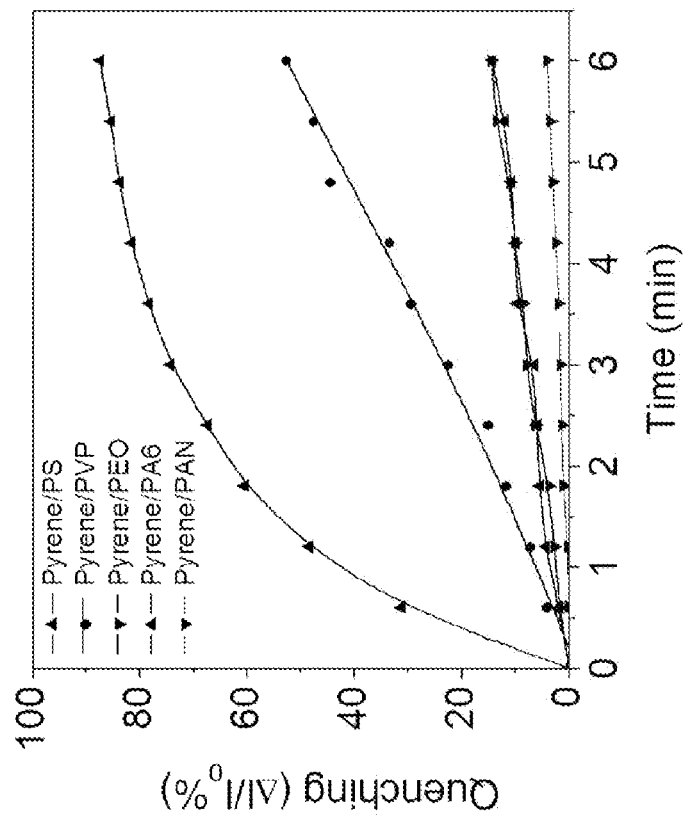
FIG. 7E is the time-dependent fluorescence quenching efficiency of the above substrates.
Figure 8A:
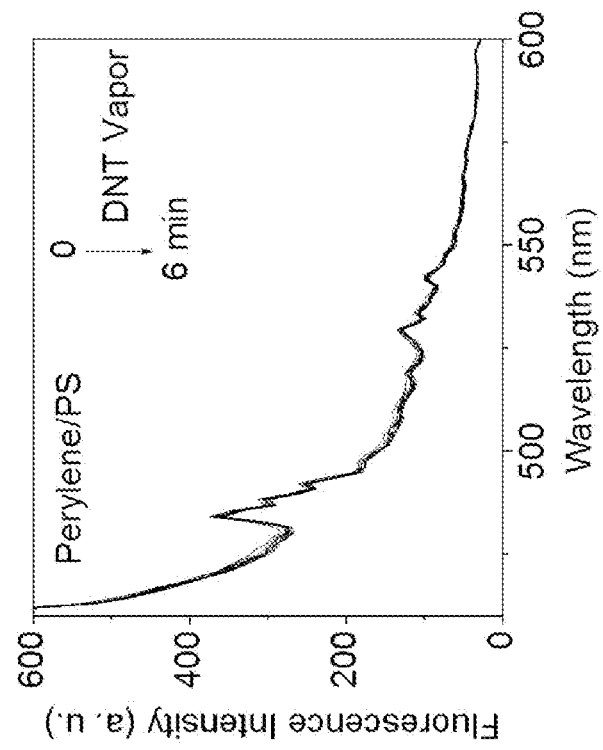
FIGS. 8A-E are fluorescence spectra of electrospun polystyrene doped with anthracene (A), perylene (B), 1-pyrenebutyric acid (C), pyrene-1-boronic acid (D) and PAHE (E), upon exposure to saturated DNT vapor (100 ppb).
Figure 8B:
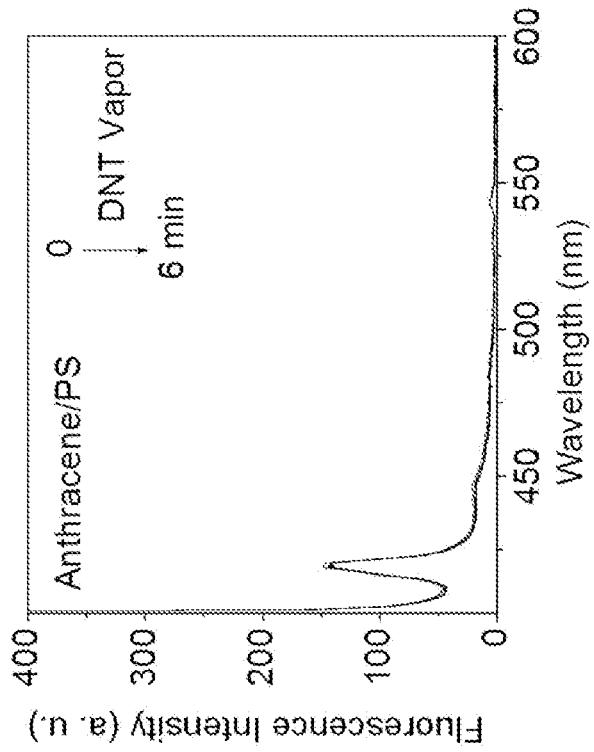
Figure 8D:
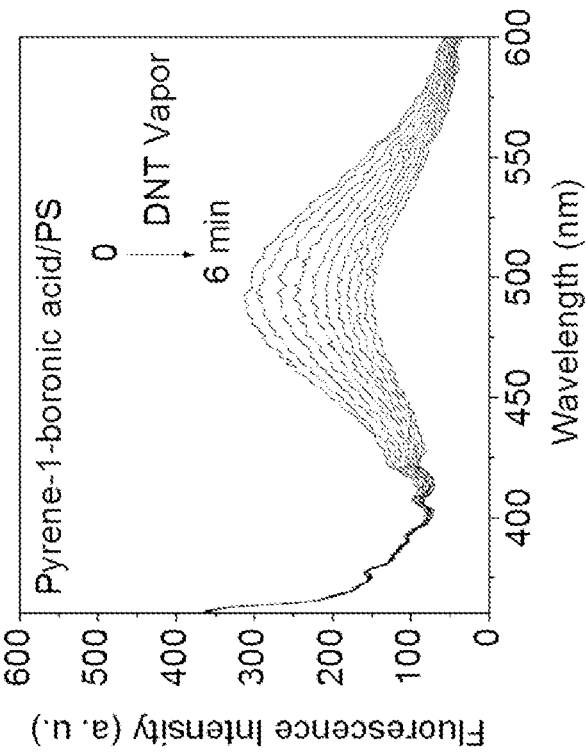
Figure 8C:
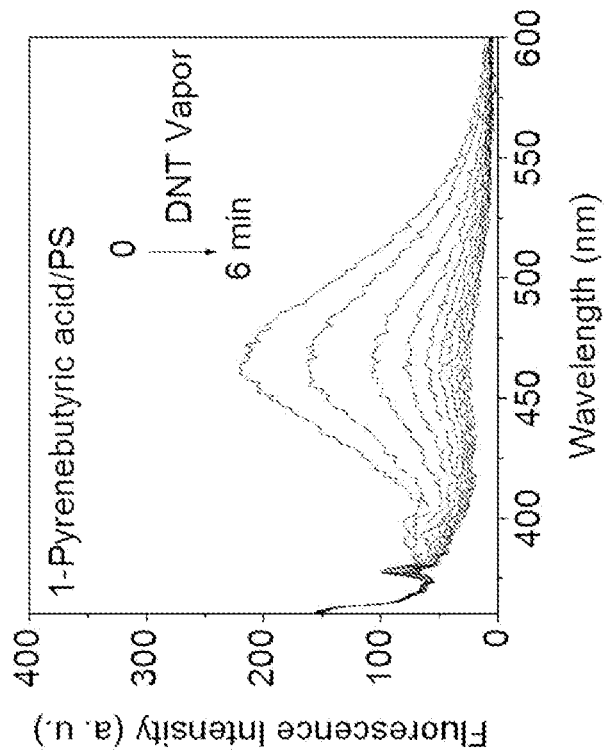
Figure 8F:
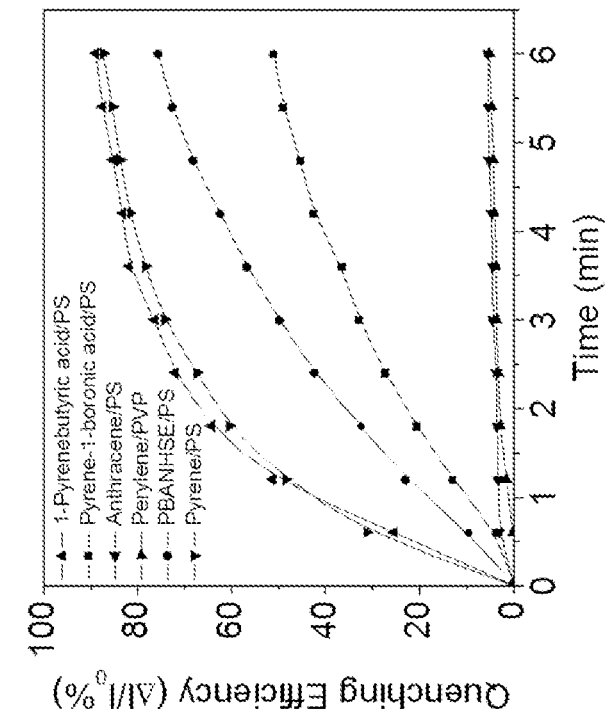
FIG. 8F is the time-dependent fluorescence quenching efficiency of the above substrates.
Figure 8E:
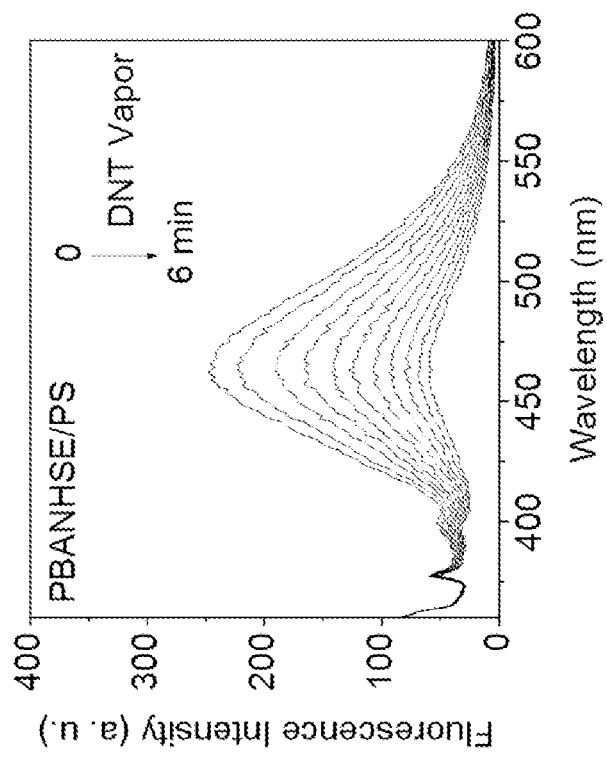

The three exemplary substrates with varying pyrene contents (2.2 wt %, 18.4 wt % and 52.9% wt) were exposed to DNT vapor (about 180 ppb) at room temperature. FIG. 5 shows the time-dependent fluorescence quenching profiles of the three different membranes upon exposure to saturated DNT vapor. The fluorescence emission features are quenched by DNT vapor for all three pyrene contents. However, the extent of quenching of the substrate containing 18.4 wt % pyrene (FIG. 5B) is larger than those containing 2.2 wt % and 52.9 wt % pyrene (FIGS. 5A and 5C, respectively). The fluorescence quenching mechanism may be ascribed to the charge-transfer between the electron-donor (pyrene) and the electron-acceptor (DNT). It is to be noted that when pyrene content is lower (2.2 wt %), the fluorescence emission and quenching are observed in the near-UV range. However, when the pyrene content is moderate (18.4 wt %) or higher (52.9 wt %), fluorescence quenching is observed at both near-UV range (likely due to the monomer) and 468 nm (likely due to the excimer). The quenching efficiency at the 468 nm wavelength is much higher. The fluorescence quenching of electrospun PS nanofibers containing 18.4 wt % pyrene exceeds 30% upon 36 seconds of exposure to saturated DNT vapor, and almost 90% quenching was reached in 6 minutes. These values are comparable to or higher than conjugated fluorescent polymers and metallophorphyrin-doped mesostructured silica film, which require complicated procedures to design, or complex chemical linking processes.

Example 3

Comparison of Dip-Coated, Spray-Coated and Spin-Cast Membranes with Electrospun Membrane As shown in FIG. 2, the pyrene/PS/TBAH nanofibrous substrates consist of numerous nanofibers with extremely high surface-to-volume ratio and high porosity, which may minimize the target molecule diffusion resistance and maximize the interaction between explosives and sensing materials. Consequently, an amplified sensing performance without significant substrate thickness dependence is achieved. To demonstrate, three control pyrene/PS/TBAH substrates were prepared by dip-coating, spray-coating and spin-casting methods, all of which have neither inner pores nor three-dimensional structure (i.e. a low porosity, and in some cases a porosity of about zero).

Three control membranes were prepared from dip-coating, spray-coating or spin-casting the pyrene/PS solution as described in Example 1. Spray-coating, dip-coating and spin-casting pyrene/PS/TBAH substrates were prepared using the same solution for electrospinning, which contains 4 wt % PS, 5 wt % TBAP and 0.1 M pyrene in THF. A spin-coating film was obtained by spinning (Laurell Technologies WS-400E-6NPP-LITE spin coater) a 50 µL solution on a glass slides (1.4 cm×3 cm) with a spin rate of 3,000 rpm. A dip-coating film was prepared by dipping a glass slide into the pyrene/PS/TBAH solution and then air drying. A spray-coating film was prepared by spraying the pyrene/PS/TBAH solution on a glass slide and then air drying.

Subsequently, the fluorescence quenching profiles as a function of the exposure time to saturated DNT vapor were recorded, and are shown in FIG. 6. FIGS. 6A-C show the fluorescence spectra of dip-coating (A), spray-coating (B), spin-casting (C) pyrene/PS membrane (pyrene content 18.4%) upon exposure to saturated DNT vapor (100 ppb). FIG. 6D shows the time-dependent fluorescence quenching efficiency of these substrates. Compared with nearly 90% fluorescence quenching efficiency achieved by the electrospun pyrene/PS membrane, much smaller and slower fluorescence quenching was observed for all control samples and less than 20% quenching efficiency could be obtained within 6 min exposure to DNT vapor. This suggests that the sensitivity of the substrate is provided, at least in part, by the electrospinning technique. Without wishing to be bound by any particular theory, it is believed that the highly porous structure and large surface to volume ratio afforded by electrospinning reduces diffusion resistance and amplifies the sensing performance. In addition, different from the three coating methods, electrospinning process involves in a high applied voltage, which could generate strong electric field, and thus might play a role in facilitating π-π stacking of pyrene/PS. Moreover, the nanofibrous membrane produced by electrospinning is a promising industrial-scale method and could make material commercially available in field testing.

Example 4

Comparison of Polystyrene to Other Electrospun Polymers

Polystyrene was chosen as the exemplary material to form substrates in many of the examples because it is commercially available, cost effective, capable of being electrospun, has negligible fluorescence emission in the wavelength region investigated, and has the requisite aromatic pendant structures. To compare, other commonly used polymers in electrospinning which do not have the requisite aromatic pendant structure (see Scheme 1) have also been employed to form substrates.

Electrospinning of fluorescent pyrene/PA6, pyrene/PVP, pyrene/PAN, and pyrene/PEO/TBAH nanofibrous films were prepared. Electrospun pyrene/PVP (MW=1,300,000) films were prepared by dissolving 10 wt % PVP and 0.1 M pyrene in ethanol and electrospinning at 13 kV applied voltage with a 8 cm collection distance and flow rate of 0.5 mL/hr. The electrospinning conditions for pyrene and the other polymer films were as follows: Pyrene/PAN (MW=150,000) films— 15 wt % PAN and 0.1 M pyrene in dimethylformamide (DMF), 20 kV applied voltage, 15 cm collection distance, and 0.4 mL/hr flow rate; and Pyrene/PEO/TBAH (MW=600,000) films—5 wt % PEO, 5% TBAH and 0.1 M pyrene in DMF, 20 kV applied voltage, 15 cm collection distance, and 0.4 mL/hr flow rate.

The performance of these structures toward detecting DNT vapor is shown in FIG. 7.

Scheme 1: Structures of tested polymers.

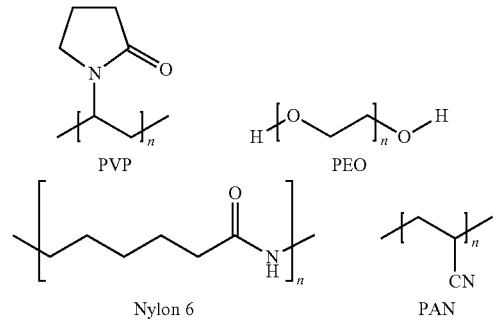

As shown in FIG. 7, after electrospinning with pyrene, all four control membranes showed weaker sensitivity and slower fluorescence quenching compared to that of electrospun pyrene/PS nanofibers. Specifically, polyethylene oxide (PEO) is a straight-chain polymer without any π-electrons in polymer backbones, thus neither π-stacking with pyrene nor long range exciton migration is possible. Consequently, the pyrene/PEO/TBAH substrate only exhibits ~15% fluorescence quenching upon 6-min exposure to 2,4-DNT vapor, which is mainly attributed to pyrene itself. Notably, electrospun pyrene/polyacrylonitrile (pyrene/PAN) showed extremely low quenching efficiency (~4% quenching at 6 min), which might result from the presence of strong electron-withdrawing nitrile groups in PAN chains and thus offer an unfavorable electrostatic interaction with electron-deficient analytes. Electrospun pyrene/polyvinylpyrrolidone (pyrene/PVP) nanofibers exhibit moderate sensitivity toward saturated 2,4-DNT vapor (~50% quenching at 6 min), possibly due to the interaction between pyrrolidone side chains of PVP and aromatic compounds which may facilitate the stacking of explosive molecules with pyrene to some extent, but the lack of π-electrons in PVP for long-range exciton migration renders PVP not as favorable as PS. TBAH is used, in part, to increase the conductivity of electrospinning solution and help generate nanoscale fibers with good morphology. The final weight percentage of TBAH in the substrate is about 45% in the as-electrospun nanofibers. The presence of the additive may provide sufficient spacing to prevent self-aggregation (self quenching) of pyrene. The electrospun pyrene/PEO/TBAH nanofibrous substrate with similar nanofiber size of pyrene/PS/TBAH nanofibrous substrate shows very limited quenching efficiency compared with that of pyrene/PS/TBAH nanofibrous substrate, indicating that the presence of TBAH itself can not explain the excellent sensing performance of pyrene/PS/TBAH nanofibrous substrate.

In addition to polystyrene, other similar electrospun aromatic polymers (e.g. aromatic biopolymers including a protein having phenylalanine residues) may be employed to form substrates with various small molecule fluorophores, including pyrene. Because of the pendant aromatic structures present in these equivalent polymers or biopolymers, it is expected that such substrates will show sensitivity to explosive materials roughly commensurate with that of electrospun pyrene/PS nanofibers.

Example 5

Comparison of Fluorophores

Various other fluorophores (pyrene, 1-pyrenebutyric acid, pyrene-1-boronic acid, 1-pyrenebutyric acid N-hydroxysuccinimide ester (PAHE), perylene and anthracene, as shown in Scheme 2) were investigated in electrospun substrates of the present teachings. The substrates comprising these different fluorophores were prepared in a similar fashion as the substrate described in Example 1.

As shown in FIG. 8, pyrene and 1-pyrenebutyric acid show the promptest quenching and highest efficiency toward DNT vapor. Pyrene-1-boronic acid and 1-pyrenebutyric acid N-hydroxysuccinimide ester also show notable quenching. Perylene and anthracene, although both very strong fluorophores, exhibited little or quenching toward DNT in the examined wavelength range. This may be due to the fact that their emission bands are very close to their adsorption range, and thus difficult to examine using common detectors.

Scheme 2: Structures of tested fluorophores

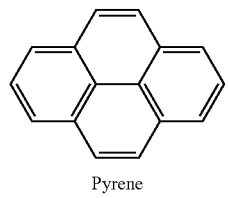

Pyrene

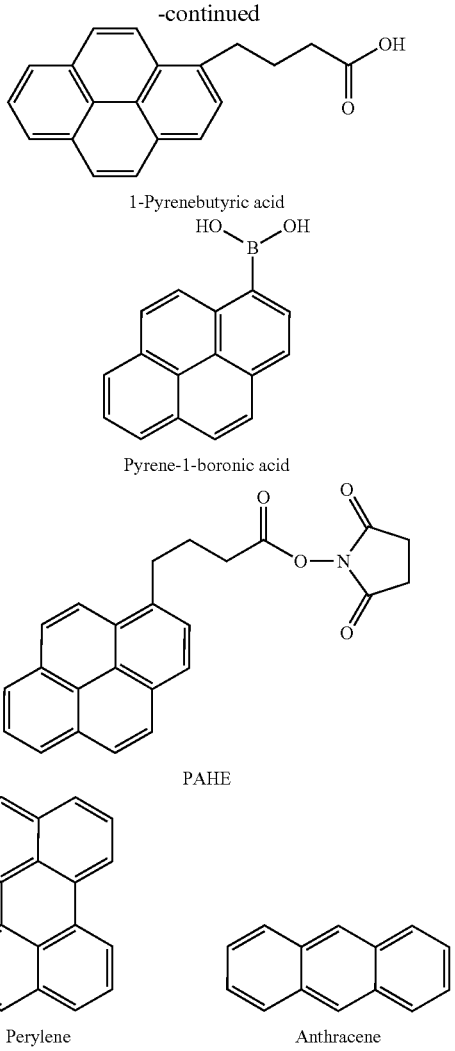

1-Pyrenebutyric acid

Pyrene-1-boronic acid

PAHE

Perylene

Anthracene

Example 6

Detection of Various Explosive Materials

Figure 9B:
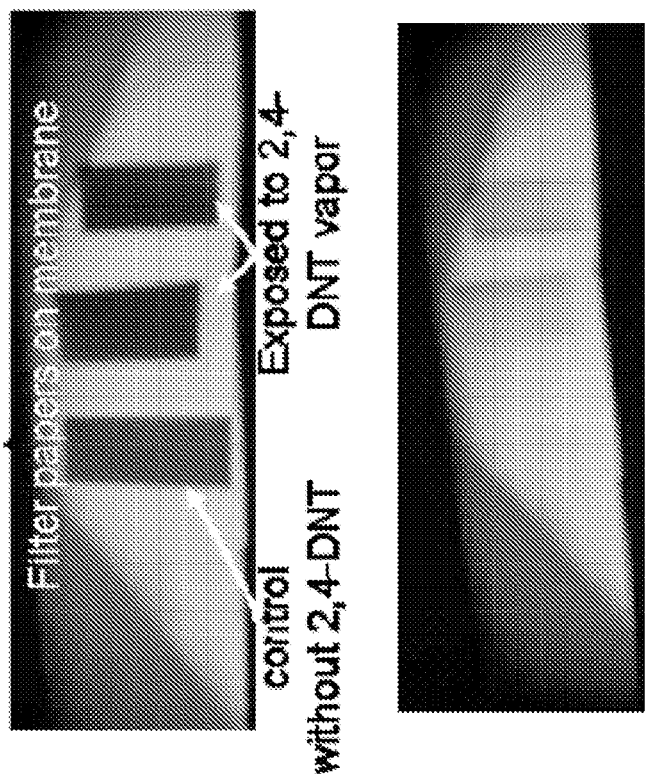
FIGS. 9A-B and 10 are photos depicting the effectiveness of exemplary explosives detection substrates of the present teaching.
Figure 9A:
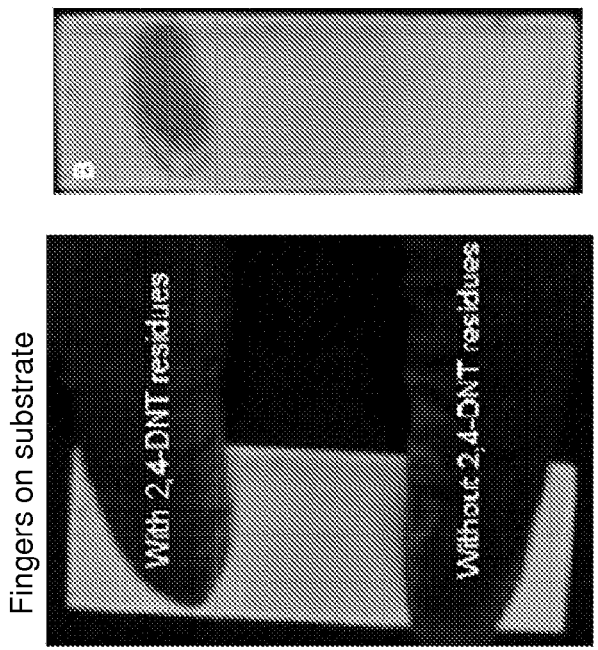

An exemplary substrate of the present teachings was prepared in accordance with Example 1. A finger was then contaminated with 2,4-DNT residue, thoroughly cleaned by tissue paper and then pressed to the substrate for less than about 5 seconds. The substrate was immediately visualized for fluorescence quenching using a handheld UV light. The results are shown in FIG. 9A (right picture). Fluorescence quenching occurs immediately on the pyrene/PS substrate and can be observed by direct visualization under handheld UV light.

An additional exemplary substrate of the present teachings was also prepared in accordance with Example 1. Two pieces of filter paper were then exposed to 2,4-DNT vapor (~180 ppb) for 15 min (although shorter times are also possible). The filter papers were then placed on the substrate for about 5 seconds and then removed. As shown in FIG. 9B (bottom picture), immediate quenching is visualized under UV light. As a comparison, no quenching effect was observed for the control filter paper.

Figure 10:
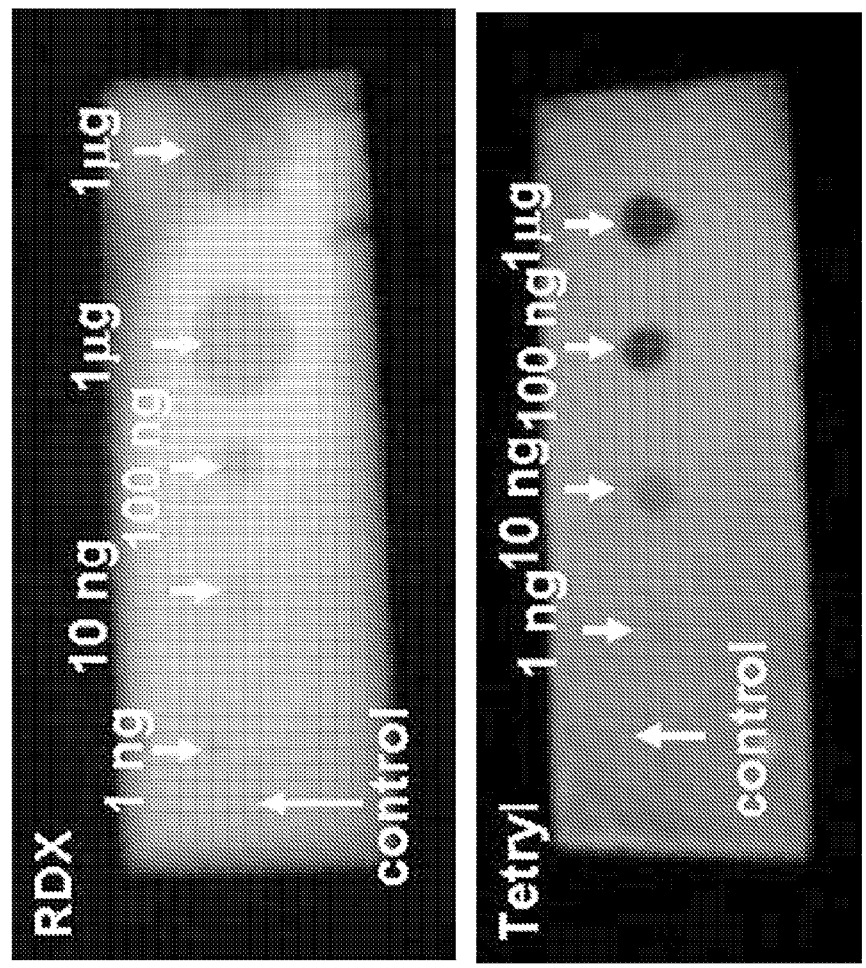

Quenching effects of different amounts of RDX and Tetryl residues were also tested on exemplary substrates prepared in accordance with Example 1. The results are presented in FIG. 10. A predetermined amount of explosive (in solvent) was dripped onto a clean glass slide. Upon evaporation of the solvent, 1 ng, 10 ng, 100 ng and 1 μg residue (RDX or Tetryl) remained. The glass slide was placed face-down on the substrate. The measurement was conducted at room temperature (without heating) and the exposure time was between 45 minutes and 2 hours, depending upon the concentration. Exposure time can be largely reduced with the use of a sensor in conjunction with the substrate. As little as 1 ng RDX and Tetryl can both be detected by direct visual observation under UV light.

Example 7

Preparation and Characterization of Another Electrospun Pyrene/PS Membrane

Another exemplary fluorescent pyrene/PS/TBAH nanofibrous film was prepared by electrospinning. A solution of 0.1 M Pyrene was added to a tetrahydrofuran (THF) solution containing 4 wt % PS ($M_w$=350,000) and 5 wt % TBAH and then stirred for 1 hr. A positive bias of 25 kV was applied to the needle using a high voltage power supply device (CZE-1000R, Spellman High Voltage Electronics Co., NY, USA), and the feeding rate for the precursor solution was set to be 0.3 mL/h by a syringe pump (KD-200, KD Scientific Inc., Holliston, Mass., USA). The electrospinning procedure was conducted under ambient conditions and the as-electrospun nanofibers were collected on a piece of aluminum foil placed 10 cm below the tip of the needle. To prepare electrospun film on glass slides or filter paper, the same procedure was applied except that clean glass slides or Whatman filter paper were placed on the top of the aluminum foil as the collectors.

Example 8

Fluorescence Quenching with 2,4-DNT, 2,6-DNT, 1,2-DNB, and 1,3-DNB Vapors

The exemplary substrate of Example 7 was exposed to different explosives vapor at room temperature. Briefly, a methacrylate cuvette with cover was filled with a small amount of solid explosive (e.g. 2,4-DNT powder) and equilibrated for 48 h to ensure saturation reached. A small piece of cotton was placed on top of the solids to avoid direct contact with the substrate. The cuvette was placed in the Varian Cary Eclipse fluorescence spectrophotometer (Agilent Technologies) and then the glass slide coated with the substrate was inserted into the cell at the 45 degree angle. The recording of the fluorescence change was started immediately after the substrate was placed in the cell, and the emission spectrum was collected every 36 s in the wavelength region of 360-600 nm with an excitation wavelength of 340 nm. The fluorescence intensities (I) were normalized to the first value recorded after exposure to the quencher vapor ($I_0$) and the quenching efficiency was defined as ($I_0$-I)/$I_0$×100%. The quenching experiments towards equilibrium vapors of other nitroaromatics (2,6-DNT, 1,2-DNB and 1,3-DNB) and controls (AN, SN, BQ and CA) were conducted in a similar way.

Figure 11A:
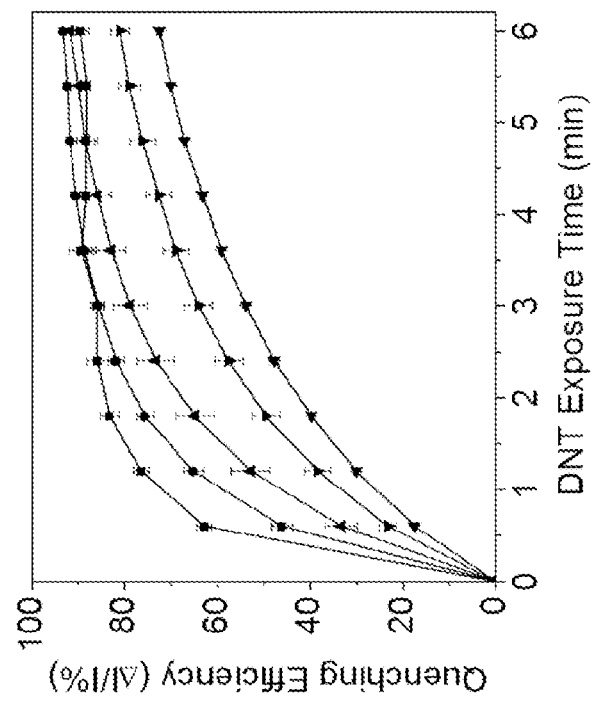
FIGS. 11A-C are plots showing the time-dependent fluorescence intensity of electrospun substrate (3-μm thick) upon exposure to explosives.
Figure 11B:
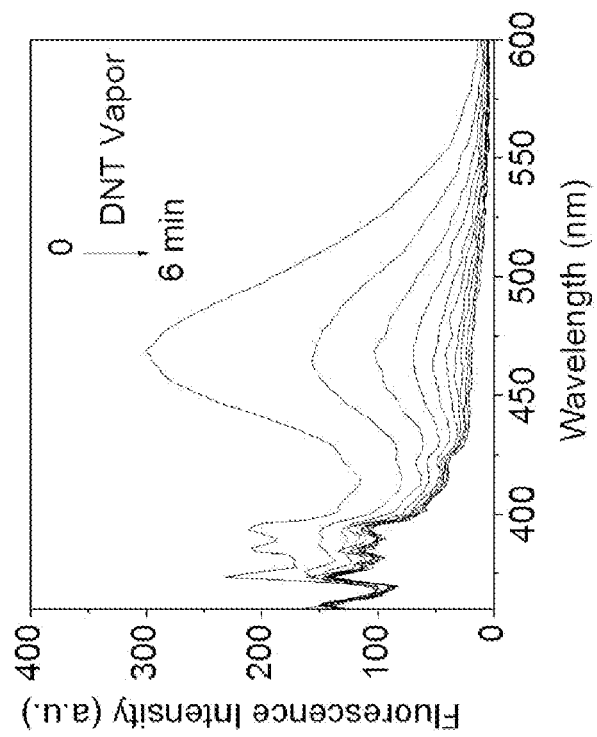
Figure 12:
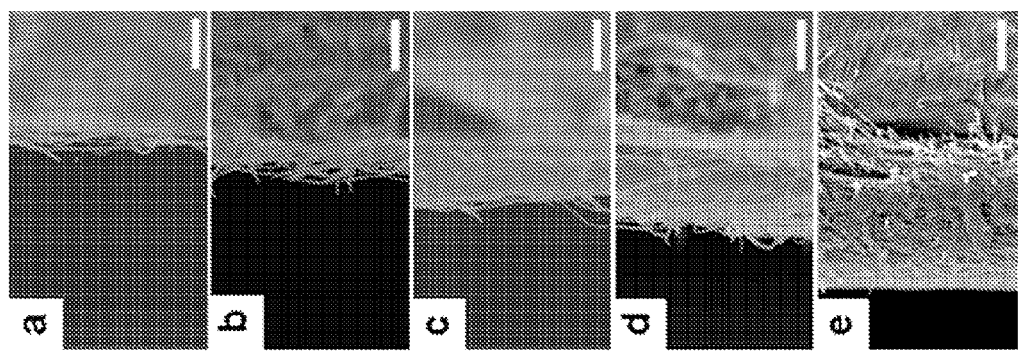
FIG. 12 shows SEM images of electrospun pyrene/PS/TBAH substrates with different collection times (from top to bottom: 30 s, 3 min, 6 min, 10 min and 20 min). Scale bars, 5 μm.
Figure 13:
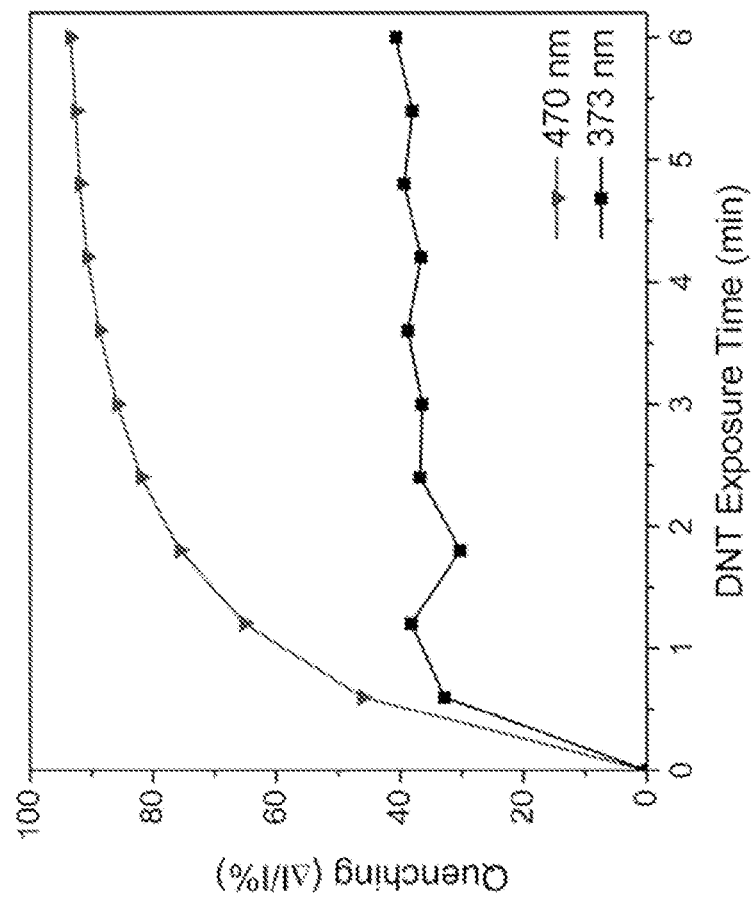
FIG. 13 is a comparison of fluorescence quenching efficiency of an electrospun pyrene/PS/TBAH substrate (3 μm thick) at monomer (373 nm) and excimer (470 nm) peaks upon exposure to equilibrium 2,4-DNT vapor.

The sensing performance of these electrospun pyrene/PS/TBAH nanofibrous substrates was applied to the detection of nitroaromatic vapors. FIG. 11A shows the time-dependent fluorescence spectra of a pyrene/PS/TBAH substrate (ca. 3 μm thickness) upon exposure to equilibrium 2,4-DNT vapor (~193 ppb). Simultaneous fluorescence quenching of both monomer (373, 385, and 393 nm) and excimer (470 nm) emission were observed with a much higher quenching efficiency at the excimer peak (see FIG. 13). Nearly 46% quenching at 470 nm could be observed at 36 seconds and more than 90% achieved within 6 minutes. The quenching mechanism may be ascribed to the electron transfer from excited pyrene to the electron-deficient nitroaromatics. The effect of substrate thickness on quenching efficiency was also investigated and presented in FIG. 11B. The quenching speed to reach a plateau was slightly decreased with the increase of substrate thickness, however, all showed a similar quenching trend. The highest quenching efficiency (93%) towards equilibrium 2,4-DNT vapor at 6 min was obtained on a 3 μm thick film, compared to 89% and 72% on 1 μm and 15 μm thick substrate, respectively, indicating that the sensing performance of the substrate is not heavily dependent on the substrate thickness. FIG. 12 shows electrospun substrates with different thicknesses which were prepared by changing the collection time (30 s, 3 min, 6 min, min, and 20 min). The film thicknesses were measured by SEM and estimated to be ca. 1 μm, 3 μm, 6 μm, 9 μm, and 15 μm, respectively.

Figure 11C:
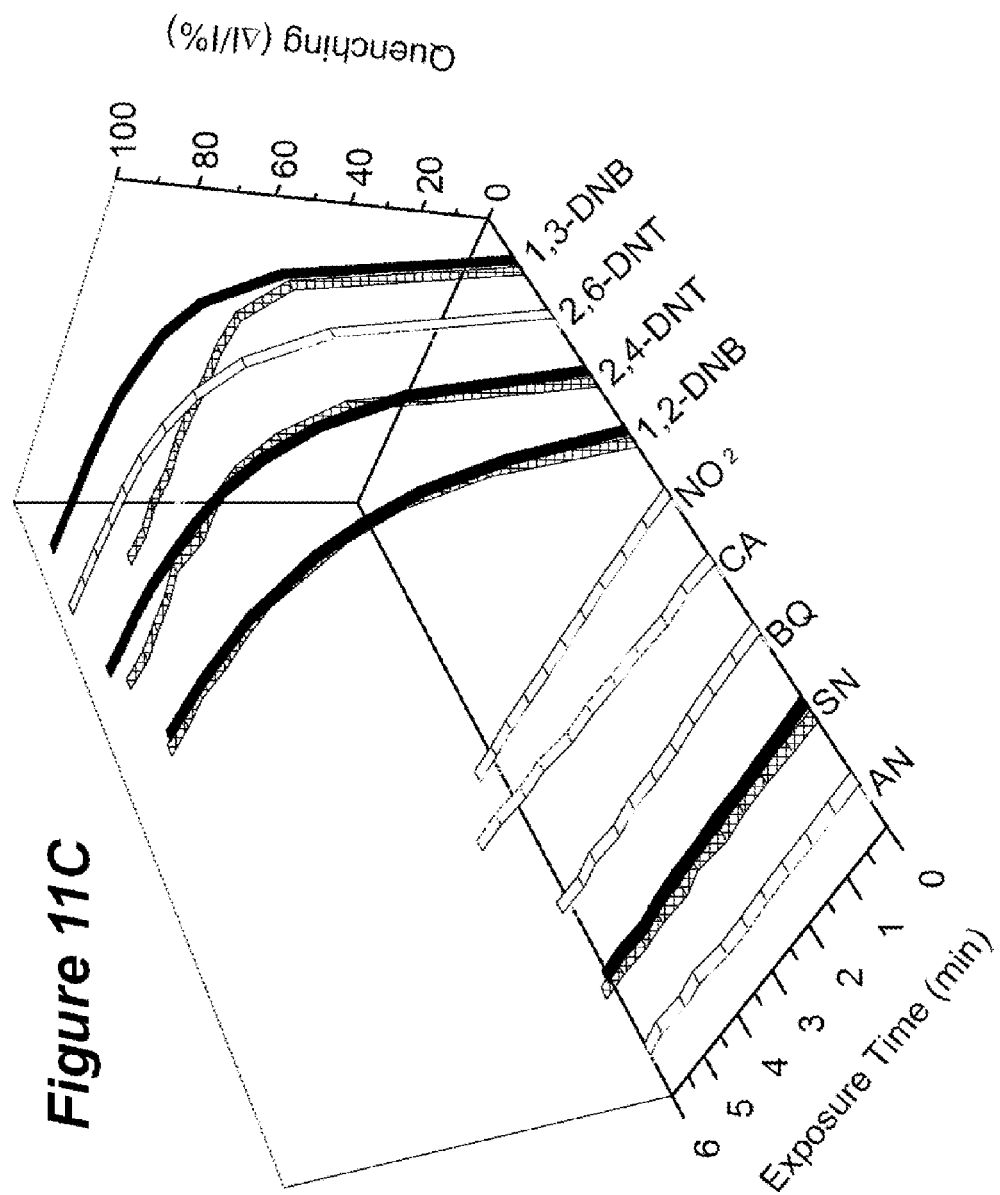

The fluorescence quenching of electrospun pyrene/PS/TBAH to equilibrium vapors of representative nitroaromatics and selected interferences is shown in FIG. 11C. Remarkable quenching efficiency was observed for all nitroaromatic vapors such as 2,4-DNT (93%), 2,6-DNT (96%), 1,2-dinitrobenzene (1,2-DNB, 81%), and 1,3-DNB (95%). Besides showing superior sensitivity comparable to leading nitroaromatic sensors in the literature, the as-electrospun pyrene/PS/TBAH substrate also possesses excellent selectivity against common interferences. Exposure to saturate vapors of inorganic nitrites ($NO_2$) and nitrates ($NO_3$), such as sodium nitrite (SN) and ammonium nitrate (AN), did not cause quenching of the substrate. The substrate can substantially differentiate nitroaromatics from common compounds used in nitrogen fertilizers. Moreover, the introduction of strong electron-acceptors, such as saturated 1,4-benzoquinone (BQ), chloranil (CA) vapors, and 50 ppm $NO_2$ gas does not result in any significant quenching of the substrate. The substrate is substantially inert to strong oxidants other than nitroexplosives.

Figure 17:
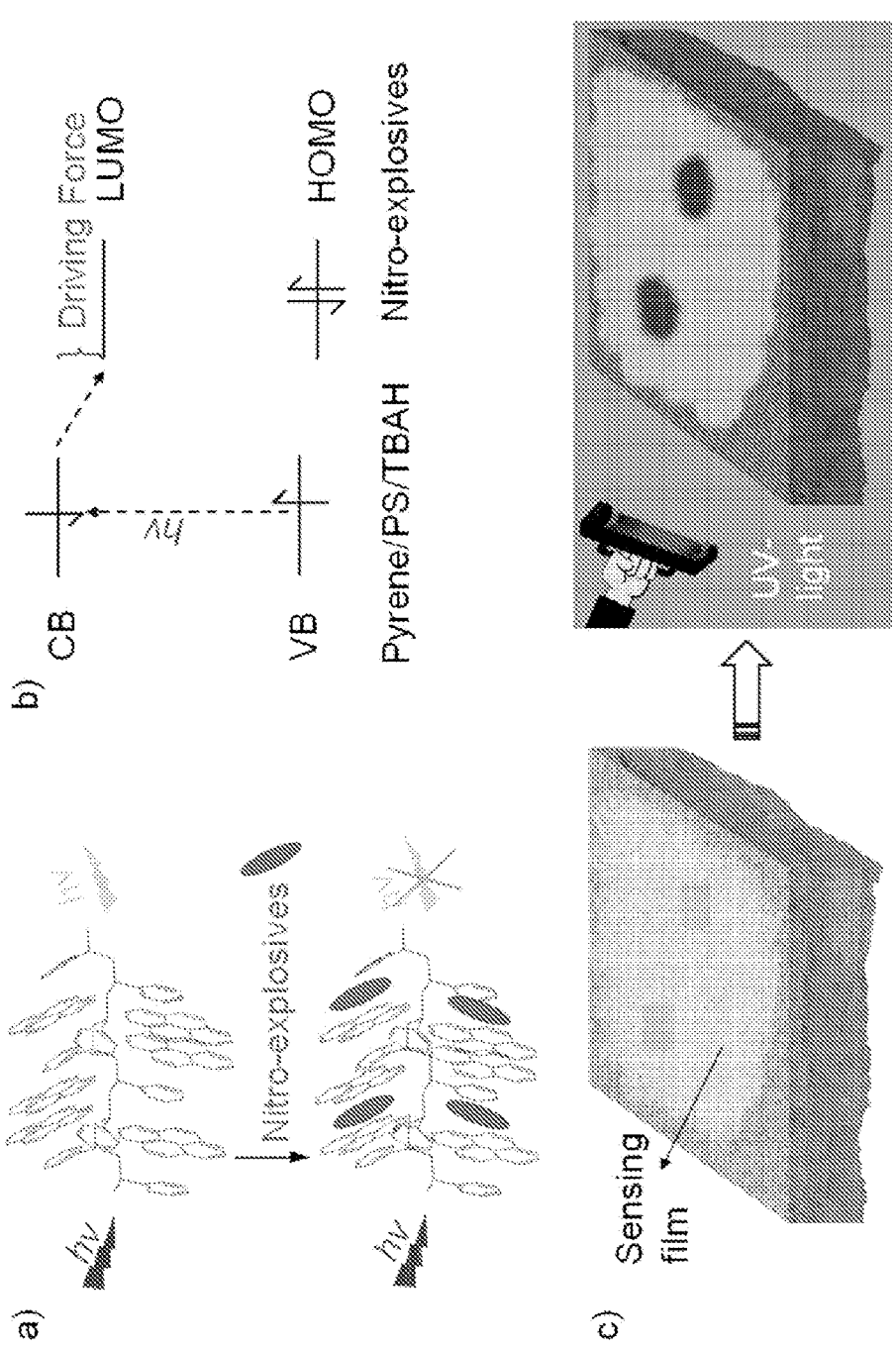
FIGS. 17A-C show one possible configuration of the present teachings as a "sandwich-like" conformation of pyrene/PS in electrospun nanofibrous substrate (top) and the potential intercalative bindings of nitro explosives (bottom) (A), a photoinduced electron transfer mechanism for electrospun pyrene/PS/TBAH substrates by nitro explosive (B), and a schematic drawing for mapping buried-explosives using a sensing substrate under a hand-held UV-light (FIG. 17C).

Previous studies have revealed that the analyte's electronic structure, vapor pressure, and binding constant to the substrate surface may be important factors in fluorescence quenching. FIG. 1 summarizes the calculated orbital energies (at B3LYP/6-31G* level), vapor pressures, and saturated vapor concentration of the analytes investigated. Since the fluorescence quenching mechanism is based, in part, on the electron-deficient nitro explosives accepting an excited-state electron from the fluorophore, a driving force for this photoinduced electron transfer process results from the energy gap between the conduction band of pyrene/PS/TBAH substrates and the lowest unoccupied molecular orbital (LUMO) of explosives (FIG. 17B). For all nitro explosives, the low LUMO energies can accept the electron from the excited state of a pyrene (an exemplary small molecule fluorophore), and as a result, the exemplary electrospun pyrene/PS/TBAH substrate may be effectively quenched. Nitroaromatic explosives, which are different from nitramine and nitrate ester explosives, have π-electrons to facilitate their, intercalative bindings with pyrene/PS and also possess relative higher volatility. Consequently, nitroaromatic explosives exhibit strong and fast quenching efficiency for electrospun substrates of the present disclosure, such as pyrene/PS/TBAH substrates. In contrast, the LUMO energies of inorganic nitrite and nitrate salts (SN, AN), as well as peroxide-based explosives TBAP, are too high for energetically favorable electron transfer, and thus insignificant fluorescence quenching of these substrates may be observed. BQ and CA have substantially lower LUMO energies and higher vapor pressures than nitro explosives, and much lower fluorescence quenching of pyrene/PS/TBAH substrate upon exposure to their saturated vapor was observed. This may result from their weaker electrostatic interactions (the average charges on each hydrogen in BQ and CA were determined from a Mulliken population analysis (6-31G*) to be +0.19 and +0.12) with the substrate and a lower surface binding constant compared with that of nitro explosives.

Example 9

Detection of Various Explosive Materials

To evaluate the utility of the as-electrospun pyrene/PS/TBAH substrate as a low-cost, disposable substrate for broad-class nitro explosive vapors, its fluorescence quenching response towards the vapors of nitramine and nitrate ester explosives was investigated. In this example, saturated vapors of nitramines and nitrate esters, such as 2,4,6-trinitrophenyl-methylnitramine (Tetryl), PETN, RDX, and octahydro-1,3,5,7-tetranitro-1,3,5,7-tetrazocine (HMX) were not directly applied due to their unavailability of solid explosives. Instead, close-up exposure (no contact) to sub-equilibrium vapor generated from freshly spotted explosive residues was used (FIG. 14A). As a comparison, 1,3,5-trinitrobenzene (TNB), TNT, and acetone peroxide (TATP) were also evaluated as representatives of nitroaromatic- and peroxide-based explosives.

Stock solutions of HMX, RDX, PETN, Tetryl, TNB, TNT, and TATP were made (all at 1,000 μg/mL in acetonitrile, except 100 μg/mL in methanol for TATP and 1,000 μg/mL in methanol for TNB). The solutions were diluted and 1 μL of each diluted explosive solution was dropped onto a glass slide. After the solvent evaporated, the explosive residue spots with different amount of explosives (e.g. 1 ng, 10 ng, 100 ng, and 1 μg) were ready for the quenching tests.

To visualize the detection of trace explosives vapor, glass slides coated with electrospun pyrene/PS/TBAH substrates were placed onto the top of the explosive spotted slides with a spacer (i.e. a copper strip, ~100 μm thick, see FIG. 14A) to avoid the direct contact between explosive particulates and substrates. A handheld UV lamp ($\lambda_{ex}$ 275 nm) was used to reveal the quenching spots (visualized by naked eyes) after a short exposure time. FIG. 14C shows the observed quenching spots.

Figure 14:
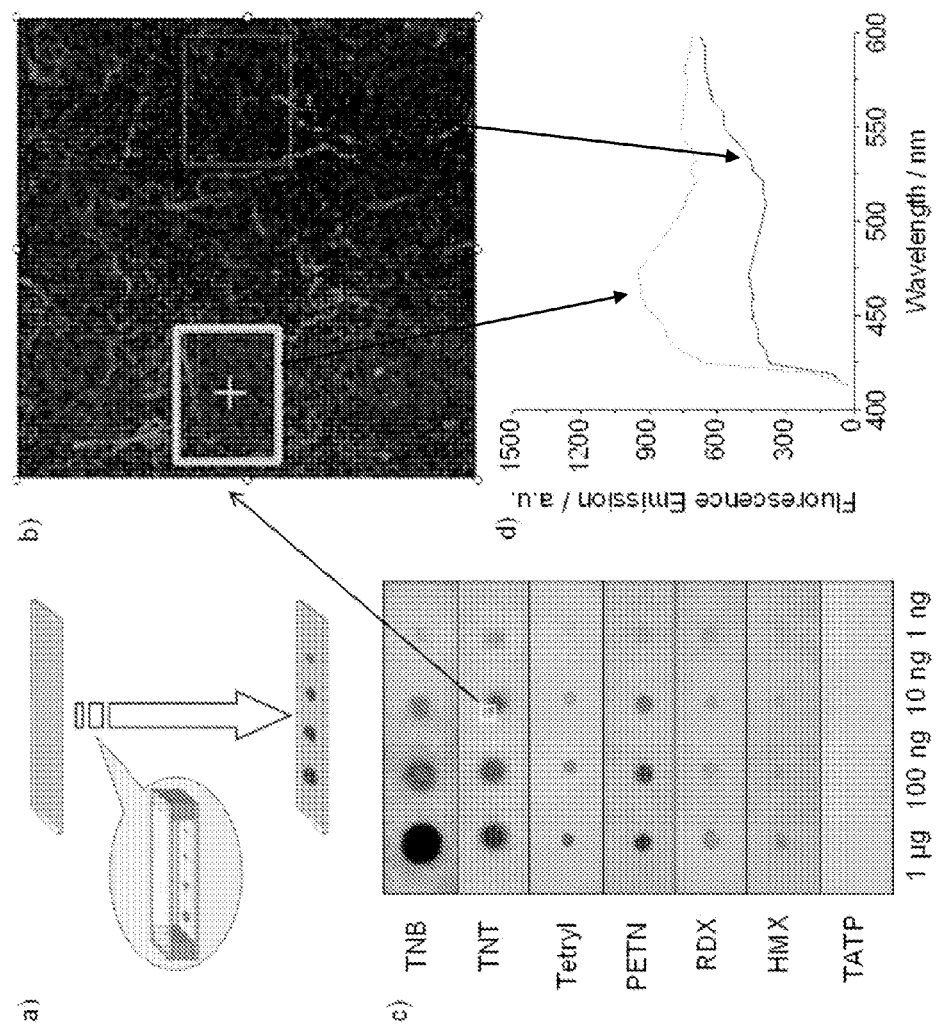
FIGS. 14A-D show a schematic illustration of an experimental setup for electrospun pyrene/PS/TBAH substrates towards sub-equilibrium nitro-explosive vapors (A), a fluorescence microscopy image ($\lambda_{ex}$ 343 nm, $\lambda_{em}$ 470 nm) at the edge of the quenching spot (B), UV excited ($\lambda_{ex}$ 275 nm) images of 3-μm thick substrates after exposure to sub-equilibrium vapors generated from 1 μg, 100 ng, 10 ng, and 1 ng solid analytes (C), and an emission profile ($\lambda_{ex}$ 343 nm) of the square area outside and inside the quenching spot (D).
Figure 15E:
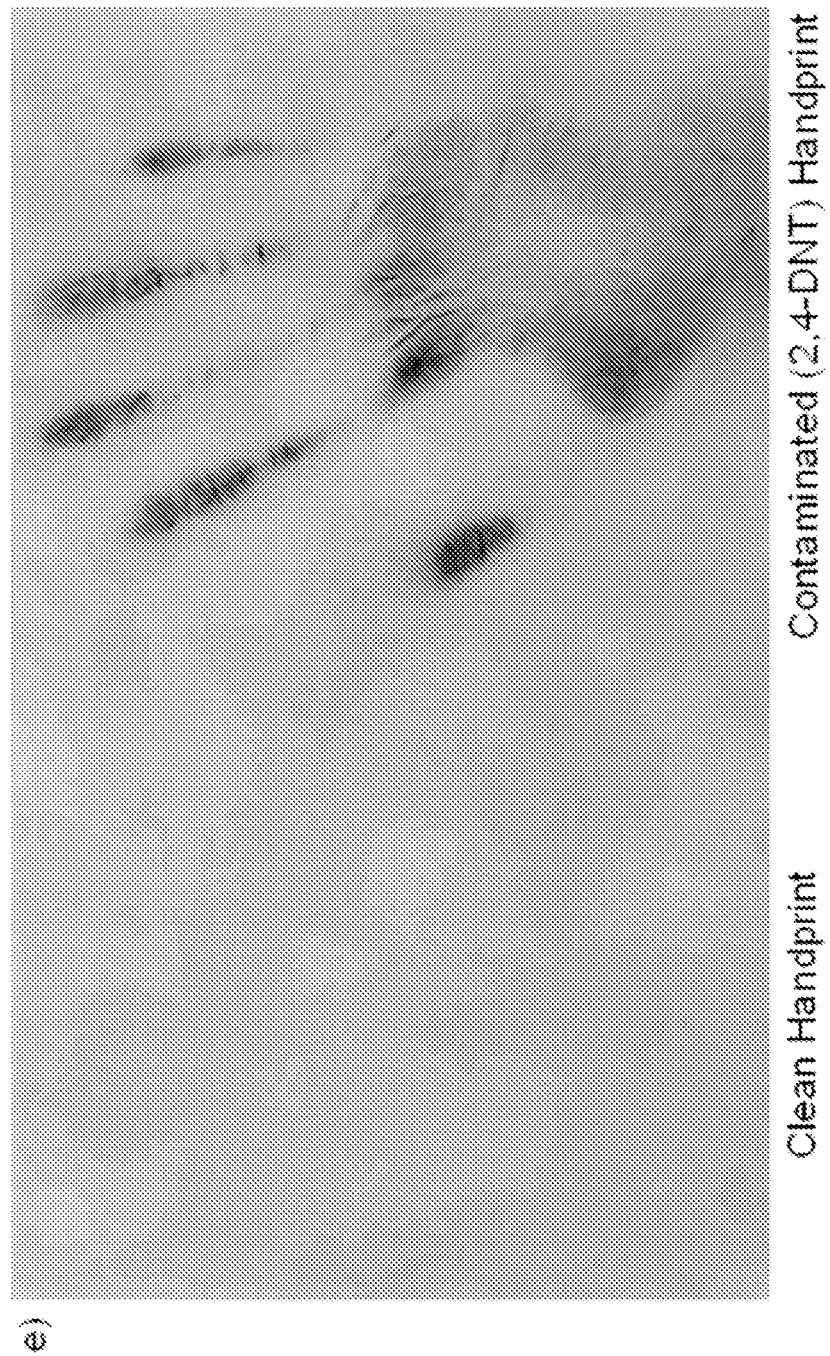

As shown in FIG. 14, all nitramine and nitrate ester explosives are discriminated by their sub-equilibrium vapors generated from nanogram residues. The sub-equilibrium vapors from 10 ng of RDX and PETN produce acceptable dark quenching circles and are visualized by naked eyes after 20 min. For RDX and PETN, 1 ng is visualized with an extended exposure time of 2 hr. The time for HMX detection took longer (~2 hr for 1 μg, and ~12 hr for 1 ng) due to its extremely low volatility. The performance of the substrate is unexpectedly superior to known method in the art, considering the fact that the tested vapors were generated from freshly spotted explosive residues in an open environment with concentrations much lower than their equilibrium or saturated vapor concentration (e.g. 0.1 ppt for HMX, 5 ppt for RDX, 7 ppt for PETN, and 74 ppt for Tetryl) and the detection was conducted without the use of any piece of advanced instrument. TNB and TNT vapors give fast and strong responses. Dark and big fluorescence quenching is observed within 10 minutes for exposure to the sub-equilibrium vapors from 1 ng residues. This may be due to their relatively higher volatility and more aromatic electrons to facilitate the π-π interaction with pyrene/PS. The quenching efficiency may also be quantitatively measured by comparing the fluorescence emission profiles outside and inside the quenching spots. FIG. 14D is the emission profile ($\lambda_x$ 343 nm) of the square area outside and inside the quenching spot in FIG. 14B. As shown in FIGS. 14C and 14D, 52% fluorescence quenching at 470 nm was generated by the sub-equilibrium vapors of 10 ng TNT (determined by comparing the fluorescence at 470 nm before and after explosive detection). In contrast, peroxide-based explosives such as TATP did not induce any fluorescence quenching due to its poor electron withdraw capability.

The quenching efficiency of the exemplary pyrene/PS/TBAH nanofibrous substrate towards 2,4-DNT vapor superior to those of conjugated polymers in literature. The as-prepared substrate is also inexpensive as compared to conjugated polymers which usually require complicated and costly synthetic routes. In addition, unlike conjugated polymers, the performance of the substrates of the present teachings do not significantly dependency on thickness. Contrary to commonly used ex-situ detection methods (the sample exposed to explosives vapor in a sealed container and then taken out for analysis), the present substrate was kept in cuvette with saturated explosives vapor for in-situ detection. Testing under such conditions may substantially reduce the signal variation and greatly improve the reliability of the data. Moreover, the most difficult to be detected explosives such as RDX, PETN, and HMX at sub-equilibrium vapors naturally released from their nanogram explosives residues were also detected by naked eyes under a UV light. No known detection method has demonstrated vapor detection of the explosives shown herein. Surprisingly, the low-cost substrate of the present teachings can detect all of these explosives due to, in part, the ultrasensitivty of the substrate for a broad spectrum of explosives. No advanced analytic instruments were relied on in testing these explosives, rather they were visualized by naked eyes with the help of an inexpensive UV lamp.

Example 10

Detection of Buried Explosives

The exemplary electrospun pyrene/PS/TBAH nanofibrous substrate was used to detect buried explosives (e.g. 2,4-DNT). Direct detection of buried explosives is the first step toward the detection and cleanup of unexploded landmines. The best way to find buried explosives (e.g. landmines) is to detect explosive molecules directly. In the field, saturated vapor concentrations are never reached as air movement causes any degree of dilution, and ppt (or below) level detection is needed.

Quenching testing for buried explosives involved burying 0.2 g of 2,4-DNT in soil in a Petri dish and a flower pot. Substrate-coated filter paper, prepared by directly electro-spinning pyrene/PS/TBAH nanofibrous substrate onto the filter paper, was placed on the top of soil with the substrate facing up. After certain reaction times, a handheld UV lamp ($\lambda_{ex}$ 275 nm) was used to "visualize" the fluorescence quenching spots by naked eyes, which indicates the position of buried explosives. FIGS. 15A-D shows the detection of explosives buried in soil using filter paper coated with the exemplary electrospun pyrene/PS/TBAH nanofibrous substrate.

By interaction with leaked explosive molecules from buried explosives, a strong fluorescence quenching can be observed (e.g. within ~10 min) by naked eyes under UV light. The quenching spots indicated the position of buried explosives, while other parts without explosives are still active.

This is first time buried explosives have been detected without the use of any advanced analytical instrumentation. Considering the low cost of the substrate and the inexpensive UV lamp used, the developed explosive substrate technology has the potential for large scale landmine mapping.

Figure 16:
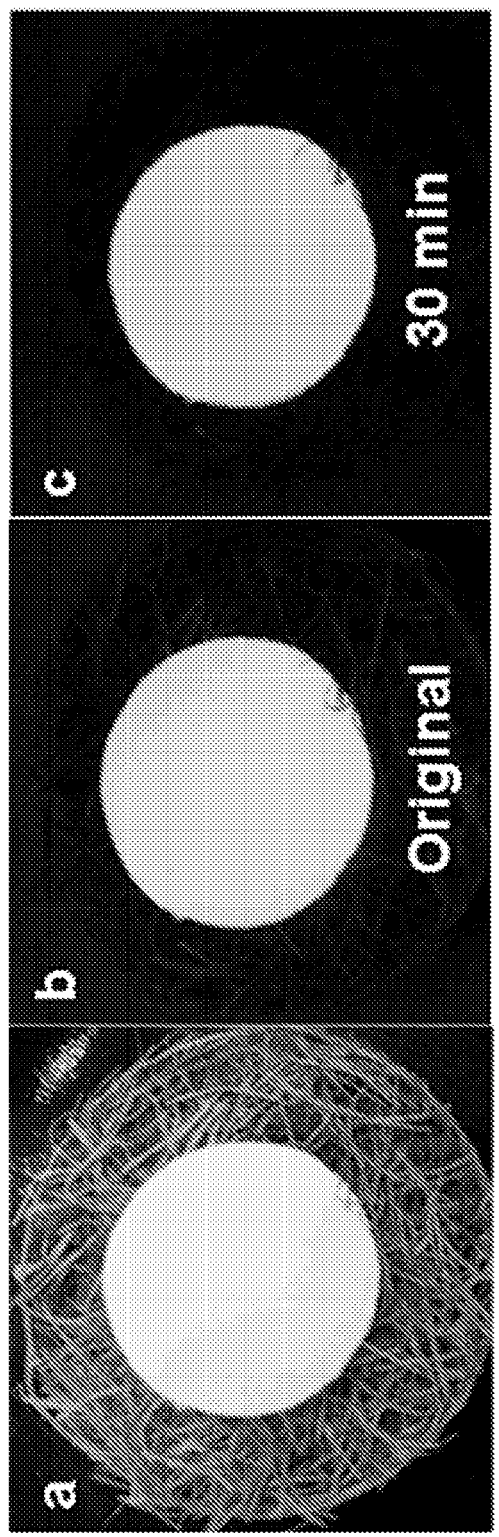
FIGS. 16A-C show optical images of an electrospun pyrene/PS/TBAH substrate on grass (A), a UV ($\lambda_{ex}$ 275 nm) excited image of electrospun sensing substrate on grass in the beginning (B), and a UV ($\lambda_{ex}$ 275 nm) excited image of electrospun sensing substrates on grass after 30 min (C). The pyrene/PS/TBAH substrates (3 μm thick) were electrospun onto a Whatman filter paper and placed face-up on the grass for 30 min. Fluorescent images were continuously taken under UV excitation ($\lambda_E$ 275 nm).

The exemplary substrate also demonstrates superior selectivity. The substrate coated filter paper sitting on the top of grass displayed no change in the fluorescence (see FIG. 16). In addition, human sweat did not cause any interference either (data not shown). As addressed above, it was also determined that common nitrogen fertilizers and oxidants show insignificant response. All of these results demonstrate that the substrate of the present teachings possess excellent selectivity against common interferences.

The detection of an explosive particulate contaminated handprint through direct contact was also demonstrated. Trace amounts of 2,4-DNT were analyzed as hand-prints (FIG. 15E) after handling a solid explosive material with nitrile gloves. The explosive residue handprint was visualized by naked eyes with a UV light. The right hand (nitrile gloved) was rubbed with 2,4-DNT powder and then wiped clean until no visible explosive particulates were left. The trace amount of DNT contaminated glove was then gently pressed (~1 s contact time) onto the electrospun pyrene/PS/TBAH substrate for visualization by naked eyes under a handheld UV light. As a comparison, a clean handprint of left hand (nitrile gloved) without 2,4-DNT contamination was simultaneously pressed onto the same sensing film.

The gloves were wiped clean until no visible explosive particulates and then gently pressed onto the electrospun pyrene/PS/TBAH nanofibrous membrane for 1 s. Under UV light, clear handprints were visualized by naked eyes right away. As a control, a hand-print without any explosives residue was simultaneously pressed onto the sensing membrane, and no visible fluorescence quenching could be observed from the control handprint. The fluorescence quenching does not come from the scratching of the direct contact, as the membrane still keeps its surface integrity after the hand-print.

Example 11

Further Characterization of the Substrate

In the exemplary substrate, PS is chosen as the polymer to dope pyrene because its phenyl side chains can enable the intercalative co-facial $\pi$-$\pi$ stacking with pyrene. The interaction is both geometrically feasible and electronically favorable. The shape-persistent geometry of the PS scaffold also serves as the spacer to prevent the excessive stacking (aggregation) of pyrene and thus minimize its self-quenching. A "sandwich-like" conformation (FIG. 17A) may be formed. It has been proposed and demonstrated that one-dimensional $\pi$-$\pi$ stacking is highly favorable for exciton transportation via co-facial intermolecular electronic coupling ("molecular wire" amplification). Analogously, the "sandwich-like" conformation between pyrene and phenyl pendants of PS in this work may lead to a facilitated long-range exciton migration and thus achieve amplified fluorescence quenching similar to "molecular wire" (FIG. 17A).

The electrospun pyrene/PS/TBAH substrates of the present teachings provide a fast, highly-sensitive and selective, and cost-effective way for the direct vapor detection towards a broad range of nitro explosives, including the most challenging ones such as RDX, PETN and HMX. The demonstration of buried explosive detection allows for large-scale unexploded landmine detection and cleanup (see FIG. 17C). The superior sensing performance may be attributed, in part, to the proposed "sandwich-like" conformation between aromatic polymer (PS) and small molecule fluorophore (pyrene) which may allow efficient long-range energy migration similar to "molecular wire", thus achieving amplified fluorescence quenching. Compared with those sophisticated fluorescence-based explosives detection systems, nanofibrous pyrene/PS/TBAH substrates prepared by electrospinning could be mass-produced with low-cost, allowing for large scale application.

EQUIVALENTS

Those skilled in the art will recognize, or be able to ascertain using no more than routine experimentation, many equivalents to the specific embodiments of the teaching described herein. Such equivalents are intended to be encompassed by the following claims. Finally, the disclosures of all cited references contained in this disclosure are incorporated herein by reference in their entireties.

We claim:

1. An explosives detecting substrate comprising:
an aromatic polymer having a pendant aromatic group; and
a fluorophore, wherein the fluorophore is non-covalently bound to the polymer and wherein the pendant aromatic group and the fluorophore form a $\pi$-$\pi$ stacking configuration,
wherein the fluorophore is present in the substrate at about 5% to about 45%, by weight; and
wherein the substrate exhibits a porosity of at least about 5%.

2. The substrate of claim 1, wherein the aromatic polymer comprises a plurality of structural units corresponding to Formula (I):

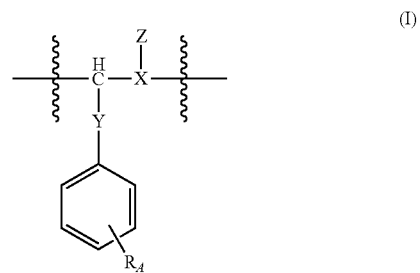

wherein $R_A$ is selected from hydrogen, cyano, methyl, —B(OH)$_2$, —C(O)H, —C(O)CH$_3$, —C(O)OH, —C(O)OCH$_3$, and SO$_3$;
wherein X is —(CH$_2$)$_n$—, n is 1-5, and at least one —(CH$_2$)— unit may be optionally replaced with a —(NH)— or and —O— group;
wherein Y is selected from a bond and —(CH$_2$)$_m$—, and m is 1-3; and
wherein Z is selected from hydrogen, methyl, ethyl, propyl, isopropyl, (O), —C(O)H, —CH$_2$—C(O)H, —C(O)CH$_3$, —C(O)OH, or —C(O)OCH$_3$.

3. The substrate of claim 2, wherein the aromatic polymer is polystyrene.

4. The substrate of claim 1, wherein the fluorophore comprises an aromatic multi-ring hydrocarbon, an aromatic multi-ring heterocycle, or a mixture thereof.

5. The substrate of claim 4, wherein the fluorophore is at least one fluorophore selected from compounds of Formula (II) or Formula (III):

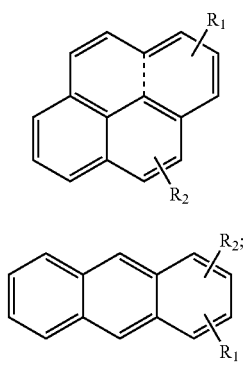

wherein $R_1$ and $R_2$ are each independently selected from hydrogen, cyano, $C_{1-4}$ alkyl, —B(OH)$_2$, —C(O)H, —$C_{1-4}$ alkyl-C(O)H, —C(O)CH$_3$, —$C_{1-4}$ alkyl-C(O)CH$_3$, —C(O)OH, —$C_{1-4}$ alkyl-C(O)OH, —C(O)OCH$_3$, —$C_{1-4}$ alkyl-C(O)OCH$_3$ and —$C_{1-4}$ alkyl-C(O)O-succinimide.

6. The substrate of claim 5, wherein the fluorophore is selected from pyrene, 1-pyrenebutyric acid, pyrene-1-boronic acid, 1-pyrenebutyric acid N-hydroxysuccinimide ester, anthracene and mixtures thereof.

7. The substrate of claim 6, wherein the fluorophore comprises pyrene.

8. The substrate of claim 1, wherein the substrate comprises a polystyrene-pyrene matrix.

9. The substrate of claim 1, wherein the aromatic polymer is in the form of electrospun or dry spun fibers, (electro) sprayed particles or fibers, or mixtures thereof.

10. The substrate of claim 1, wherein the substrate exhibits a surface to volume ratio of at least about 1 mm$^2$/mm$^3$.

11. The substrate of claim 1, wherein the substrate is capable of detecting an explosive material in an amount less than about 1 ppb.

12. The substrate of claim 1, wherein the substrate is capable of detecting an explosive material having a vapor pressure of less than about $1\times10^{-5}$ Torr at room temperature/atmospheric pressure.

13. The substrate of claim 1, wherein the substrate is capable of detecting an explosive material in less than about 6 minutes.

14. A method for detecting an explosive material, the method comprising:
contacting the explosives detecting substrate of claim 1 with an explosive material for at least about 1 second;
measuring the amount of fluorescence emitted by the explosives detecting substrate; and
comparing the amount of fluorescence of the explosives detecting substrate with a control substrate that has not been exposed to the explosive material;
wherein an explosive material is detected where the fluorescence of the explosives detecting substrate is less than the fluorescence of the control substrate.

15. The method of claim 14, wherein the explosive material comprises a low vapor pressure explosive material.

16. The method of claim 14, wherein the explosive material comprises at least one explosive selected from octahydro-1,3,5,7-tetranitro-1,3,5,7-tetrazocine (HMX), hexahydro-1,3,5-trinitro-1,3,5-triazine (RDX), 1,3,5-trinitrobenzene (TNB), 1,3-dinitrobenzene (DNB), methyl-2,4,6-trinitrophenylnitramine (Tetryl), nitrobenzene (NB), 2,4,6-trinitrotoluene (TNT), picric acid (PA), 2,4-dinitrotoluene (24DNT), 2,6-dinitrotoluene (26DNT), o-nitrotoluene (2NT), m-nitrotoluene (3NT), p-nitrotoluene (4NT), nitroglycerin (NG), 4-amino-2,6-dinitrotoluene (4-Am-DNT), 2-amino-4,6-dinitrotoluene (2-Am-DNT), pentaerythritol tetranitrate (PETN) and 2,3-dimethyl-2,3-dinitrobutane (DMNB).

17. The method of claim 14, wherein the method is capable of detecting an explosive material in an amount less than about 1 ppb.

18. A sensor comprising the explosives detecting substrate of claim 1.

19. The sensor of claim 18, further comprising a complementary analytical device.

20. The sensor of claim 19, wherein the complementary analytical device is at least one device selected from a fluorimeter, a mass spectrometer and an absorption spectrometer.

21. The substrate of claim 1, further comprising an organic salt, wherein the salt is selected from the group consisting of tetrabutylammonium hexafluorophosphate (TBAP), sodium 1-heptene-2-sulfonate, ammonium bromide, 1-naphthyl phosphate calcium salt trihydrate, ammonium hexafluorophosphate, tetramethylammonium hexafluorophosphate, and tetrabutylammonium hydroxide 30-hydrate.

22. The substrate of claim 21, wherein the salt is tetrabutylammonium hexafluorophosphate (TBAP).

23. The substrate of claim 22, wherein TBAP is present in the substrate at about 45%, by weight.

24. The substrate of claim 1, wherein the π-π stacking configuration produces long-range exciton migration and amplified fluorescence quenching compared to a substrate without a π-π stacking configuration.

25. An explosives detecting substrate comprising:
an aromatic polymer having a pendant aromatic group in the form of electrospun or dry spun fibers, (electro) sprayed particles or fibers, or mixtures thereof; and
a fluorophore, wherein the fluorophore is non-covalently bound to the polymer, wherein the pendant aromatic group and the fluorophore form a π-π stacking configuration and wherein the fluorophore is present in the substrate at about 5% to about 45%, by weight.

26. A method for forming an explosives detecting substrate, the method comprising:
electrospinning, dry spinning or (electro)spraying an aromatic polymer having a pendant aromatic group in the presence of a fluorophore wherein the fluorophore is present in the substrate at about 5% to about 45%, by weight, and wherein the pendant aromatic group and the fluorophore form a π-π stacking configuration;
such that an explosives detecting substrate is formed.

27. The method according to claim 26, wherein electrospinning is used to form the substrate, and wherein the electrospinning step comprises the application of a voltage, wherein the voltage ranges from about 0 to about 25 kV.

* * * * *